(12) United States Patent
Baltz et al.

(10) Patent No.: US 6,521,406 B1
(45) Date of Patent: Feb. 18, 2003

(54) SPNG, A GENE FOR SPINOSYN INSECTICIDE BIOSYNTHESIS

(75) Inventors: Richard H. Baltz, Indianapolis, IN (US); M. Christine Broughton, Indianapolis, IN (US); Kathryn P. Crawford, Indianapolis, IN (US); Krishnamurthy Madduri, Woodlawn, OH (US); Donald J. Merlo, Carmel, IN (US); Patti J. Treadway, Greenwood, IN (US); Jan R. Turner, Carmel, IN (US); Clive Waldron, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/603,207

(22) Filed: Jun. 23, 2000

Related U.S. Application Data

(62) Division of application No. 09/370,700, filed on Aug. 9, 1999, now Pat. No. 6,274,350, which is a division of application No. 09/036,987, filed on Mar. 9, 1998, now Pat. No. 6,143,526.

(51) Int. Cl.[7] .................................................. C12Q 1/68
(52) U.S. Cl. .................... 435/6; 435/320.1; 435/252.3; 435/325; 435/254.11; 435/419; 536/23.2
(58) Field of Search ..................... 536/23.1, 23.2; 435/320.1, 252.3, 76, 6, 254.11, 325, 419

(56) References Cited

U.S. PATENT DOCUMENTS

| | | | |
|---|---|---|---|
| 4,874,748 A | 10/1989 | Katz et al. | 514/29 |
| 4,935,340 A | 6/1990 | Baltz et al. | 435/6 |
| 5,149,638 A | 9/1992 | Beckmann et al. | 435/76 |
| 5,252,474 A | 10/1993 | Gewain et al. | 435/172.3 |
| 5,614,619 A | 3/1997 | Pieperberg et al. | 536/23 |
| 5,672,497 A | 9/1997 | Cox et al. | 435/320.1 |

FOREIGN PATENT DOCUMENTS

| | | |
|---|---|---|
| DE | 199 57 268 A1 * | 3/2001 |
| EP | 0 791 655 A | 8/1997 |
| WO | WO87/03907 | 7/1987 |
| WO | WO93/06219 | 4/1993 |
| WO | WO93/13663 | 7/1993 |

OTHER PUBLICATIONS

M. Inouye et al., "A gene encoding mycinamicin III O–methyltransferase from *Micromonospora griseorubida*," 1994, *Gene 141*: 121–124.

M. Geistlich et al., "Characterization of a novel regulatroy gene governing the expression of a polyketide syntase gene in *Streptomyces ambofaciens*," 1992, *Molecular Microbiology 6*: 2019–2029.

S. Donadio et al., "Modular Organization of Genes Required for Compley Polyketide Biosynthesis," 1991, *Science 252*: 675–679.

Donadio et al., "Organization of the enzymatic domains in the multifunctional polyketide synthase involved in erythromycin formation in *Saccharopolyspora erythraea*," 1992, *Gene 111*: 51–60.

Siggaard–Anderson, "Conserved residues in condensing enzyme domains of fatty acid syntases and related sequences," 1993, *Protein Seq Data Anal. 5*: 325–335.

Baltz et al., "Applications of transposition mutagenesis in antibiotic producing streptomycetes," 1997, *Antonie van Leeuwenhoek 71*: 179–187.

Donadio et al., "An erythromycin analog produced by reprogramming of polyketide synthesis," 1993, *Proc. Natl. Acad. Sci. USA 90*: 7119–7123.

Ruan et al., "Acyltransferase Domain Substitutions in Erythromycin Polyketide Synthase Yield Novel Erythromycin Derivatives," 1997, *J. Bacteriol. 179*: 6416–6425.

* cited by examiner

*Primary Examiner*—Ponnathapu Achutamurthy
*Assistant Examiner*—Kathleen Kerr
(74) *Attorney, Agent, or Firm*—Donald R. Stuart

(57) ABSTRACT

Spinosyn biosynthetic genes from *Saccharopolyspora spinosa*, spinosyn producing microorganisms transformed with the biosynthetic genes, methods using the biosynthetic genes to increase production of spinosyn insecticidal macrolides, and methods using the genes or fragments thereof to change the products produced by spinosyn-producing microorganisms are provided.

6 Claims, 6 Drawing Sheets

SPNG, A GENE FOR SPINOSYN INSECTICIDE BIOSYNTHESIS

This application is a divisional of application Ser. No. 09/370,700, filed Aug. 9, 1999, U.S. Pat. No. 6,274,350, which is a divisional of application Ser. No. 09/036,987, filed Mar. 9, 1998, U.S. Pat. No. 6,143,526.

SUMMARY OF THE INVENTION

The present invention provides novel biosynthetic genes, vectors incorporating the biosynthetic genes, *Saccharopolyspora spinosa* strains transformed with the biosynthetic genes, methods using these genes to increase production of spinosyn insecticidal macrolides, and methods using the genes or fragments thereof to change the products produced by spinosyn-producing strains of *Saccharopolyspora spinosa*.

BACKGROUND OF THE INVENTION

As disclosed in U.S. Pat. No. 5,362,634, fermentation product A83543 is a family of related compounds produced by *Saccharopolyspora spinosa*. The known members of this family have been referred to as factors or components, and each has been given an identifying letter designation. These compounds are hereinafter referred to as spinosyn A, B, etc. The spinosyn compounds are useful for the control of arachnids, nematodes and insects, in particular Lepidoptera and Diptera species, and they are quite environmentally friendly and have an appealing toxicological profile. Tables 1 and 2 identify the structures of a variety of known spinosyn compounds:

TABLE 1

| Factor | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| spinosyn A | H | $CH_3$ | (a) | $C_2H_5$ | $CH_3$ | $CH_3$ | $CH_3$ |
| spinosyn B | H | $CH_3$ | (b) | $C_2H_5$ | $CH_3$ | $CH_3$ | $CH_3$ |
| spinosyn C | H | $CH_3$ | (c) | $C_2H_5$ | $CH_3$ | $CH_3$ | $CH_3$ |
| spinosyn D | $CH_3$ | $CH_3$ | (a) | $C_2H_5$ | $CH_3$ | $CH_3$ | $CH_3$ |
| spinosyn E | H | $CH_3$ | (a) | $CH_3$ | $CH_3$ | $CH_3$ | $CH_3$ |
| spinosyn F | H | H | (a) | $C_2H_5$ | $CH_3$ | $CH_3$ | $CH_3$ |
| spinosyn G | H | $CH_3$ | (d) | $C_2H_5$ | $CH_3$ | $CH_3$ | $CH_3$ |
| spinosyn H | H | $CH_3$ | (a) | $C_2H_5$ | H | $CH_3$ | $CH_3$ |
| spinosyn J | H | $CH_3$ | (a) | $C_2H_5$ | $CH_3$ | H | $CH_3$ |
| spinosyn K | H | $CH_3$ | (a) | $C_2H_5$ | $CH_3$ | $CH_3$ | H |
| spinosyn L | $CH_3$ | $CH_3$ | (a) | $C_2H_5$ | $CH_3$ | H | $CH_3$ |
| spinosyn M | H | $CH_3$ | (b) | $C_2H_5$ | $CH_3$ | H | $CH_3$ |
| spinosyn N | $CH_3$ | $CH_3$ | (b) | $C_2H_5$ | $CH_3$ | H | $CH_3$ |
| spinosyn O | $CH_3$ | $CH_3$ | (a) | $C_2H_5$ | $CH_3$ | $CH_3$ | H |

TABLE 1-continued

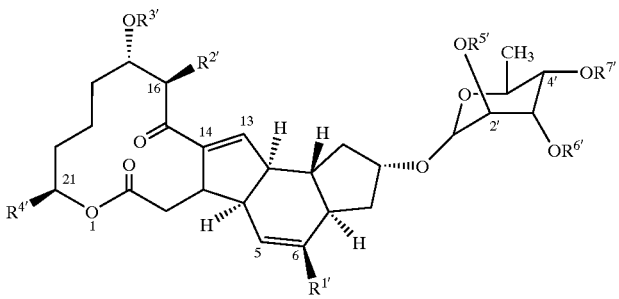

| Factor | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| spinosyn P | H | $CH_3$ | (a) | $C_2H_5$ | $CH_3$ | H | H |
| spinosyn Q | $CH_3$ | $CH_3$ | (a) | $C_2H_5$ | H | $CH_3$ | $CH_3$ |
| spinosyn R | H | $CH_3$ | (b) | $C_2H_5$ | H | $CH_3$ | $CH_3$ |
| spinosyn S | H | $CH_3$ | (a) | $CH_3$ | H | $CH_3$ | $CH_3$ |
| spinosyn T | H | $CH_3$ | (a) | $C_2H_5$ | H | H | $CH_3$ |
| spinosyn U | H | $CH_3$ | (a) | $C_2H_5$ | H | $CH_3$ | H |
| spinosyn V | $CH_3$ | $CH_3$ | (a) | $C_2H_5$ | H | $CH_3$ | H |
| spinosyn W | $CH_3$ | $CH_3$ | (a) | $C_2H_5$ | $CH_3$ | H | H |
| spinosyn Y | H | $CH_3$ | (a) | $CH_3$ | $CH_3$ | $CH_3$ | H |
| spinosyn A 17-Psa | H | $CH_3$ | H | $C_2H_5$ | $CH_3$ | $CH_3$ | $CH_3$ |
| spinosyn D 17-Psa | $CH_3$ | $CH_3$ | H | $C_2H_5$ | $CH_3$ | $CH_3$ | $CH_3$ |
| spinosyn E 17-Psa | H | $CH_3$ | H | $CH_3$ | $CH_3$ | $CH_3$ | $CH_3$ |
| spinosyn F 17-Psa | H | H | H | $C_2H_5$ | $CH_3$ | $CH_3$ | $CH_3$ |
| spinosyn H 17-Psa | H | $CH_3$ | H | $C_2H_5$ | H | $CH_3$ | $CH_3$ |
| spinosyn J 17-Psa | H | $CH_3$ | H | $C_2H_5$ | $CH_3$ | H | $CH_3$ |
| spinosyn L 17-Psa | $CH_3$ | $CH_3$ | H | $C_2H_5$ | $CH_3$ | H | $CH_3$ |

TABLE 2

| Factor | $R^{1'}$ | $R^{2'}$ | $R^{3'}$ | $R^{4'}$ | $R^{5'}$ |
|---|---|---|---|---|---|
| spinosyn A 9-Psa | H | $CH_3$ | | $C_2H_5$ | H |
| spinosyn D 9-Psa | $CH_3$ | $CH_3$ | (a) | $C_2H_5$ | H |
| spinosyn A Aglycone | H | $CH_3$ | H | $C_2H_5$ | H |
| spinosyn D Aglycone | $CH_3$ | $CH_3$ | H | $C_2H_5$ | H |

(where (a) in the $R^{5'}$ column is the dimethylamino sugar structure shown)

The naturally produced spinosyn compounds consist of a 5,6,5-tricylic ring system, fused to a 12-membered macrocyclic lactone, a neutral sugar (rhamnose) and an amino sugar (forosamine) (see Kirst et al. (1991). If the amino sugar is not present the compounds have been referred to as the pseudoaglycone of A, D, etc., and if the neutral sugar is not present then the compounds have been referred to as the reverse pseudoaglycone of A, D, etc. A more preferred nomenclature is to refer to the pseudoaglycones as spinosyn A 17-Psa, spinosyn D 17-Psa, etc., and to the reverse pseudoaglycones as spinosyn A 9-Psa, spinosyn D 9-Psa, etc.

The naturally produced spinosyn compounds may be produced via fermentation from cultures NRRL 18395, 18537, 18538, 18539, 18719, 18720, 18743 and 18823. These cultures have been deposited and made part of the stock culture collection of the Midwest Area Northern Regional Research Center, Agricultural Research Service, United States Department of Agriculture, 1815 North University Street, Peoria, Ill., 61604.

U.S. Pat. No. 5,362,634 and corresponding European Patent Application No. 375316 A1 disclose spinosyns A, B, C, D, E, F, G, H, and J. These compounds are disclosed as being produced by culturing a strain of the novel microorganism *Saccharopolyspora spinosa* selected from NRRL 18395, NRL 18537, NRRL 18538, and NRRL 18539.

WO 93/09126 disclosed spinosyns L, M, N, Q, R, S, and T. Also disclosed therein are two spinosyn J producing strains: NRRL 18719 and NRRL 18720, and a strain that produces spinosyns Q, R, S, and T: NRRL 18823.

WO 94/20518 and U.S. Pat. No. 5,6704,486 disclose spinosyns K, O, P, U, V, W, and Y, and derivatives thereof. Also disclosed is spinosyn K-producing strain NRRL 18743.

A challenge in producing spinosyn compounds arises from the fact that a very large fermentation volume is required to produce a very small quantity of spinosyns. It is highly desired to increase spinosyn production efficiency and thereby increase availability of the spinosyns while reducing their cost. A cloned fragment of DNA containing genes for spinosyn biosynthetic enzymes would enable duplication of genes coding for rate limiting enzymes in the production of spinosyns. This could be used to increase yield in any circumstance when one of the encoded activities limited synthesis of the desired spinosyn. A yield increase of this type was achieved in fermentations of *Streptomyces fradiae* by duplicating the gene encoding a rate-limiting methyltransferase that converts macrocin to tylosin (Baltz et al., 1997).

Cloned biosynthetic genes would also provide a method for producing new derivatives of the spinosyns which may have a different spectrum of insecticidal activity. New derivatives are desirable because, although known spinosyns inhibit a broad spectrum of insects, they do not control all pests. Different patterns of control may be provided by biosynthetic intermediates of the spinosyns, or by their derivatives produced in vivo, or by derivatives resulting from their chemical modification in vitro. Specific intermediates (or their natural derivatives) could be synthesized by mutant strains of *S. spinosa* in which certain genes encoding enzymes for spinosyn biosynthesis have been disrupted. Such strains can be generated by integrating, via homologous recombination, a mutagenic plasmid containing an internal fragment of the target gene. Upon plasmid integration, two incomplete copies of the biosynthetic gene are formed, thereby eliminating the enzymatic function it encoded. The substrate for this enzyme, or some natural derivative thereof, should accumulate upon fermentation of the mutant strain.

Such a strategy was used effectively to generate a strain of *Saccharopolyspora erythraea* producing novel 6-deoxyerythromycin derivatives (Weber & McAlpine, 1992).

Novel intermediates could also be synthesized by mutant strains of *S. spinosa* in which parts of certain genes encoding enzymes for spinosyn biosynthesis have been replaced with parts of the same gene which have been specifically mutated in vitro, or with corresponding parts of genes from other organisms. Such strains could be generated by swapping the target region, via double homologous recombination, with a mutagenic plasmid containing the new fragment between non-mutated sequences which flank the target region. The hybrid gene would produce protein with altered functions, either lacking an activity or performing a novel enzymatic transformation. A new derivative would accumulate upon fermentation of the mutant strain. Such a strategy was used to generate a strain of *Saccharopolyspora erythraea* producing a novel anhydroerythromycin derivative (Donadio et al., 1993).

Biosynthesis of spinosyns proceeds via stepwise condensation and modification of 2- and 3-carbon carboxylic acid precursors, generating a linear polyketide that is cyclized and bridged to produce the tetracyclic aglycone. Pseudoaglycone (containing tri-O-methylated rhamnose) is formed next, then di-N-methylated forosamine is added to complete the biosynthesis (Broughton et al., 1991). Other macrolides, such as the antibiotic erythromycin, the antiparasitic avermectin and the immunosuppressant rapamycin, are synthesized in a similar fashion. In the bacteria producing these compounds, most of the macrolide biosynthetic genes are clustered together in a 70–80 kb region of the genome (Donadio et al., 1991; MacNeil et al., 1992; Schwecke et al., 1995). At the centers of these clusters are 3–5 highly conserved genes coding for the very large, multifunctional proteins of a Type I polyketide synthase (PKS). Together the polypeptides form a complex consisting of an initiator module and several extender modules, each of which adds a specific acyl-CoA precursor to a growing polyketide chain, and modifies the β-keto group in a specific manner. The structure of a polyketide is therefore determined by the composition and order of the modules in the PKS. A module comprises several domains, each of which performs a specific function. The initiator module consists of an acyl transferase (AT) domain for addition of the acyl group from the precursor to an acyl carrier protein (ACP) domain. The extender modules contain these domains, along with a p-ketosynthase (KS) domain that adds the pre-existing polyketide chain to the new acyl-ACP by decarboxylative condensation. Additional domains may also be present in the extender modules to carry out specific β-keto modifications: a β-ketoreductase (KR) domain to reduce the β-keto group to a hydroxyl group, a dehydratase (DH) domain to remove the hydroxyl group and leave a double bond, and an enoyl reductase (ER) domain to reduce the double bond and leave a saturated carbon. The last extender module terminates with a thioesterase (TE) domain that liberates the polyketide from the PKS enzyme in the form of a macrocyclic lactone.

Macrolides are derived from macrocyclic lactones by additional modifications, such as methylation and changes in reductive state, and the addition of unusual sugars. Most of the genes required for these modifications, and for the synthesis and attachment of the sugars, are clustered around the PKS genes. The genes encoding deoxysugar biosynthetic enzymes are similar in producers of macrolide antibiotics, such as erythromycin and tylosin (Donadio et al., 1993; Merson-Davies & Cundliffe, 1994), and producers of extracellular polysaccharides, such as the O-antigens of Salmonella and Yersinia (Jiang et al., 1991; Kessler et al., 1993). All these syntheses involve activation of glucose by the addition of a nucleotide diphosphate, followed by dehydration, reduction and/or epimerization. The resultant sugar could undergo one or more modifications such as deoxygenation, transamination and methylation, depending upon the type of sugar moiety present in the macrolide. The sugars are incorporated into macrolides by the action of specific glycosyltransferases. Genes involved in the synthesis and attachment of a sugar may be tightly clustered—even transcribed as a single operon—or they may be dispersed (Decker & Hutchinson, 1993; Jarvis & Hutchinson, 1994). Spinosyn synthesis also involves bridging of the lactone nucleus, an activity that is rare in macrolide producers. Therefore, the spinosyn biosynthetic cluster may uniquely contain additional genes encoding enzymes for this function.

The following terms are used herein as defined below:

AmR—the apramycin resistance-conferring gene.
ApR—the ampicillin resistance-conferring gene.
ACP—acyl carrier protein.
AT—acyltransferase.
bp—base pairs.
Cloning—the process of incorporating a segment of DNA into a recombinant DNA cloning vector and transforming a host cell with the recombinant DNA.
CmR—the chloramphenicol resistance-conferring gene.

Codon bias—the propensity to use a particular codon to specify a specific amino acid. In the case of *S. spinosa*, the propensity is to use a codon having cytosine or guanine as the third base.

Complementation—the restoration of a mutant strain to its normal phenotype by a cloned gene.

Conjugation—a process in which genetic material is transferred from one bacterial cell to another.

cos—the lambda cohesive end sequence.

Cosmid—a recombinant DNA cloning vector which is a plasmid that not only can replicate in a host cell in the same manner as a plasmid but also can be packaged into phage heads.

DH—dehydratase.

ER—enoyl reductase.

Exconjugant—recombinant strain derived from a conjugal mating.

Gene—a DNA sequence that encodes a polypeptide.

Genomic Library—a set of recombinant DNA cloning vectors into which segments of DNA, representing substantially all DNA sequences in a particular organism have been cloned.

Homology—degree of similarity between sequences

Hybridization—the process of annealing two single stranded DNA molecules to form a double stranded DNA molecule, which may or may not be completely base paired.

In vitro packaging—the in vitro encapsulation of DNA in coat protein to produce a virus-like particle that can introduce DNA into a host cell by infection kb—kilo base pairs.

KR—β-keto reductase.

KS—ketosynthase.

Mutagenesis—creation of changes in DNA sequence. They can be random or targeted, generated in vivo or in vitro. Mutations can be silent, or can result in changes in the amino acid sequence of the translation product which alter the properties of the protein and produce a mutant phenotype.

NmR—the neomycin resistance-conferring gene.

ORF—open reading frame.

ori—a plasmid origin of replication (oriR) or transfer (oriT).

PKS—polyketide synthase.

Promoter—a DNA sequence that directs the initiation of transcription.

Recombinant DNA cloning vector—any autonomously replicating or integrating agent, including, but not limited to, plasmids, comprising a DNA molecule to which one or more additional DNA molecules can be or have been added.

Recombinant DNA methodology—technologies used for the creation, characterization, and modification of DNA segments cloned in recombinant DNA vectors.

Restriction fragment—any linear DNA molecule generated by the action of one or more restriction enzymes.

Spinosyn—a fermentation product typically characterized by a 5,6,5-tricylic ring system, fused to a 12-membered macrocyclic lactone, a neutral sugar (rhamnose) and an amino sugar (forosamine), or a similar macrocyclic lactone fermentation product produced by a microorganism utilizing all or most of the spinosyn genes.

Spinosyn genes—the DNA sequences that encode the products required for spinosyn biosynthesis, more specifically the genes spnA, spnB, spnC, spnD, spnE, spnF, spnG, spnH, spnI, spnJ, spnK, spnL, spnM, spnN, spnO, spnP, spnQ, spnR, spnS, *S. spinosa* gtt, *S spinosa* gdh, *S. spinosa* epi, and *S. spinosa* kre, as described hereinafter, or functional equivalents thereof.

Subclone—a cloning vector with an insert DNA derived from another DNA of equal size or larger.

TE—thioesterase.

Transformation—the introduction of DNA (heterologous or homologous) into a recipient host cell that changes the genotype and results in a change in the recipient cell.

BRIEF DESCRIPTION OF THE INVENTION

Figure 1A:
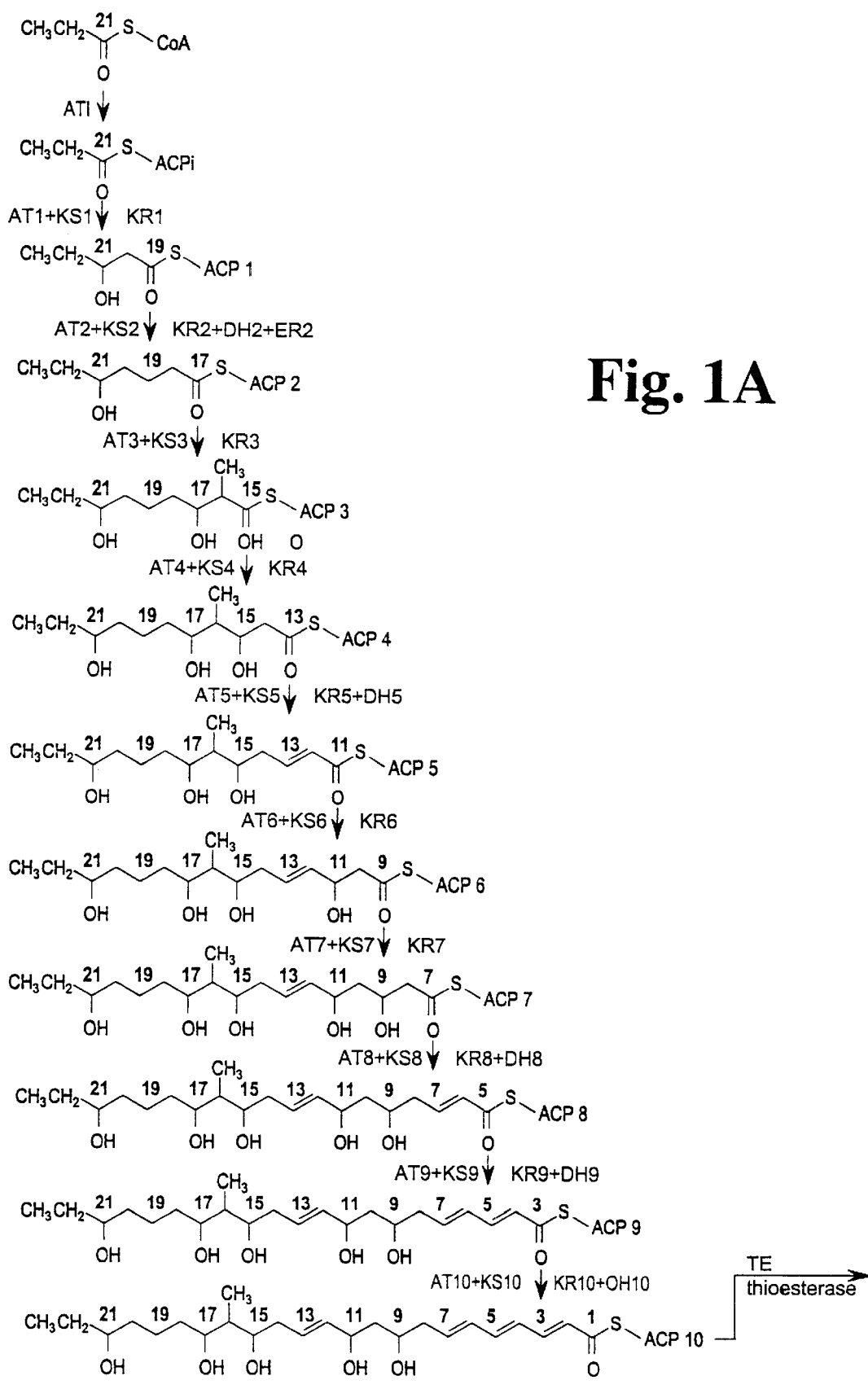
FIGS. 1A, 1B, and 1C are a diagram illustrating the spinosyn biosynthetic pathway.
Figure 1B:
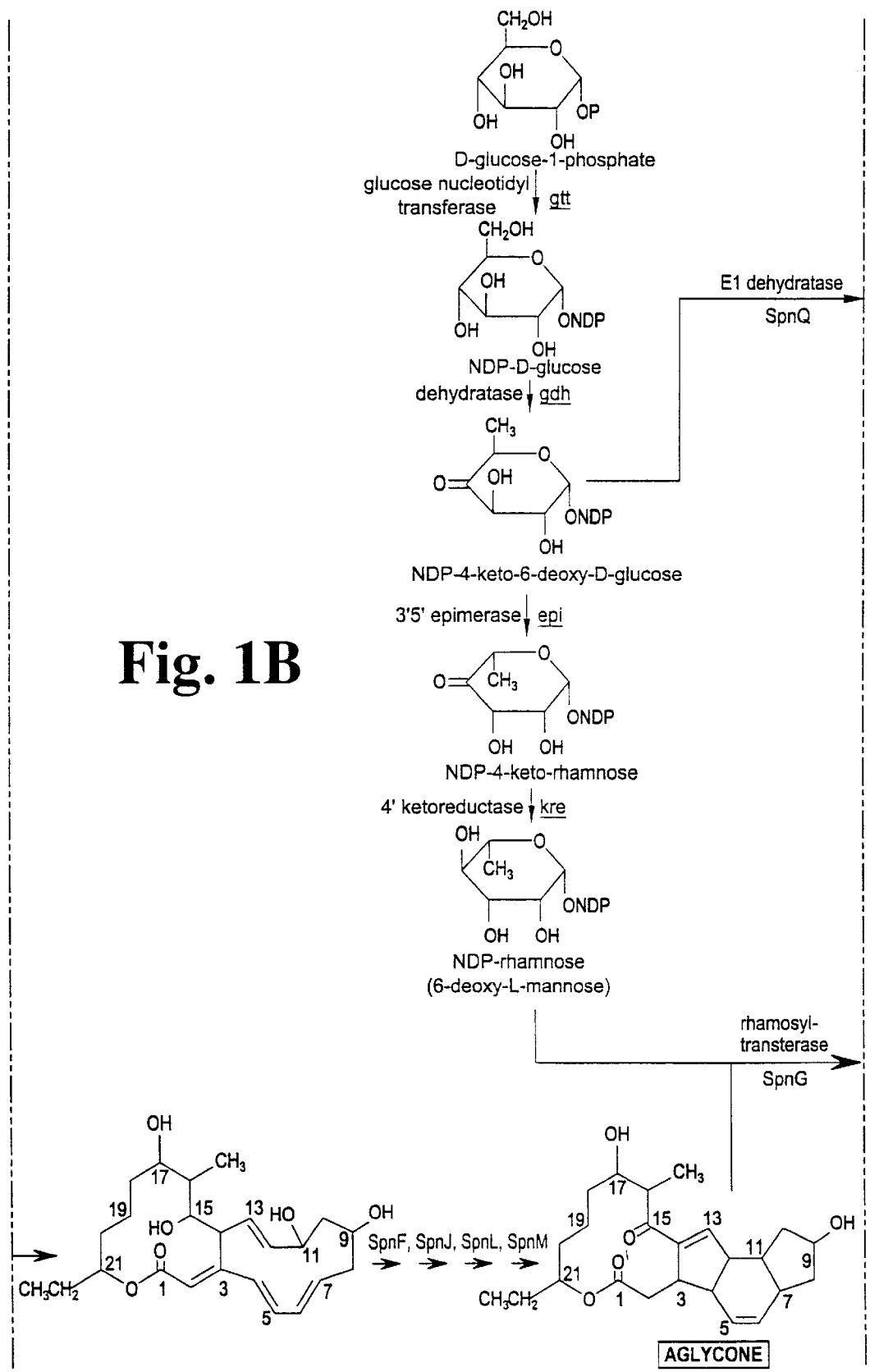
Figure 1C:
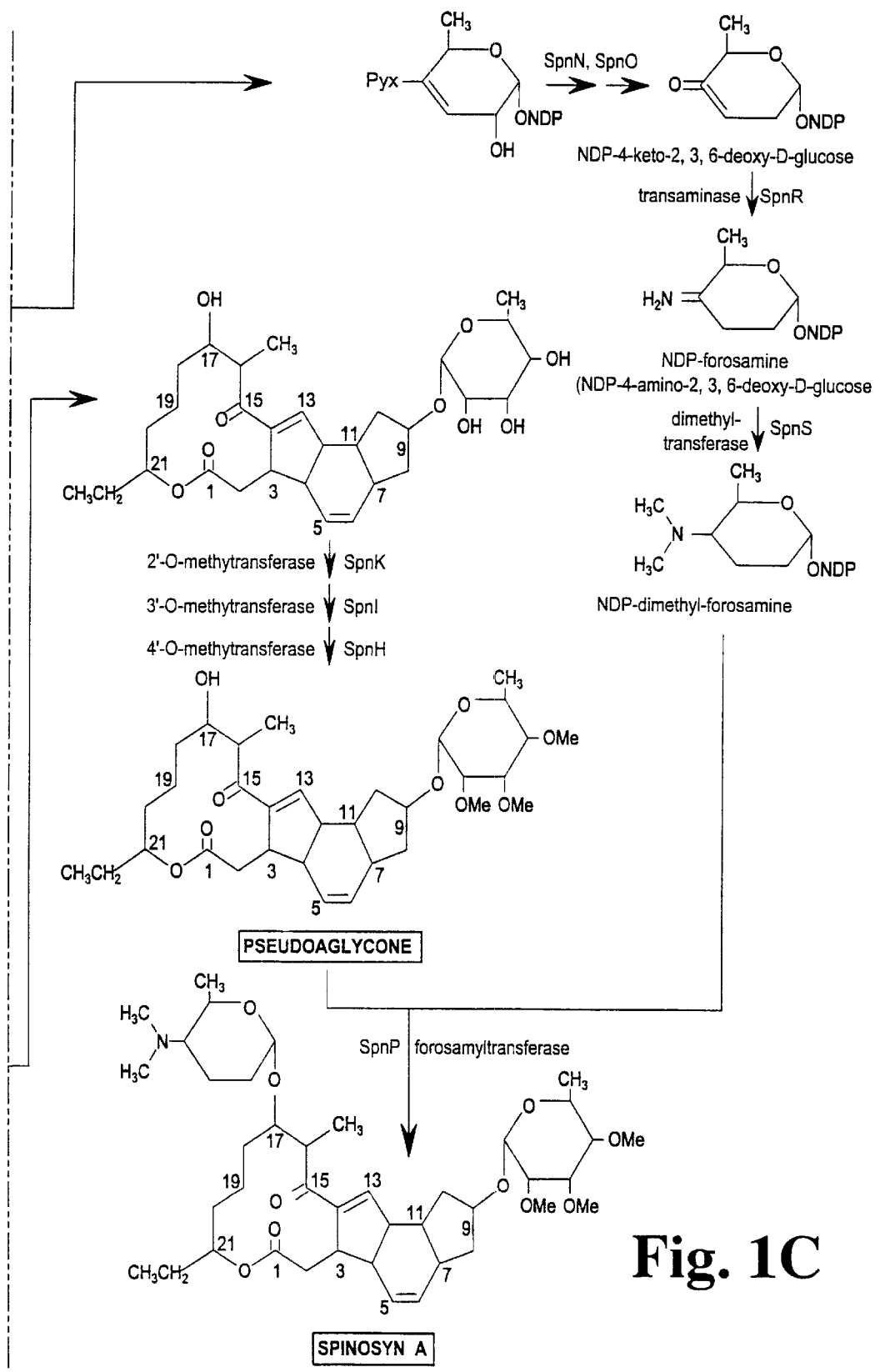

Spinosyn biosynthetic genes and related ORFs were cloned and the DNA sequence of each was determined. The cloned genes and ORFs are designated hereinafter as spnA, spnB, spnC, spnD, spnE, spnF, spnG, spnH, spnI, spnJ, spnK, spnL, spnM, spnN, spnO, spnP, spnQ, spnR, spnS, ORFL15, ORFL16, ORFR1, ORFR2, *S. spinosa* gtt, *S. spinosa* gdh, *S. spinosa* epi, and *S. spinosa* kre. The proposed functions of the cloned genes in spinosyn biosynthesis are identified FIG. 1 and in the discussion hereinafter.

In one of its aspects, the invention provides an isolated DNA molecule comprising a DNA sequence that encodes a spinosyn biosynthetic enzyme, wherein said enzyme is defined by an amino acid sequence selected from the group consisting of SEQ ID NOS 2–5, 7–24, 26, 27, 29, and 33, or said enzyme is defined by one of said amino acid sequences in which one or more amino acid substitutions have been made that do not affect the functional properties of the encoded enzyme. In a preferred embodiment, the DNA sequence is selected from the group of genes consisting of spnA, spnB, spnC, spnD, spnE, spnF, spnG, spnH, spnI, spnJ, spnK, spnL, spnM, spnN, spnO, spnP, spnQ, spnR, spnS, ORFL15, ORFL16, ORFR1, ORFR2, *S. spinosa* gtt, *S. spinosa* gdh, *S. spinosa* epi, and *S. spinosa* kre, said genes being described by, respectively, bases 21111–28898, 28916–35374, 35419–44931, 44966–59752, 59803–76569, 20168–20995, 18541–19713, 17749–18501, 16556–17743, 14799–16418, 13592–14785, 12696–13547, 11530–12492, 10436–11434, 8967–10427, 7083–8450, 5363–6751, 4168–5325, 3416–4165, 2024–2791, 1135–1971, 76932–77528 and 77729–79984 of SEQ ID NO:1, bases 334–1119 of SEQ ID NO:27, bases 88–1077 of SEQ ID NO 24, bases 226–834 of SEQ ID NO 31, and bases 1165–1992 of SEQ ID NO:24.

In another of its aspects, the invention provides an isolated DNA molecule comprising a DNA sequence that encodes a spinosyn PKS domain selected from KSi, ATi, ACPi, KS1, AT1, KR1, and ACP1, said domains being described by, respectively, amino acids 6–423, 528–853, 895–977, 998–1413, 1525–1858, 2158–2337, and 2432–2513 of SEQ ID NO:2. In a preferred embodiment, the DNA sequence is selected from the group consisting of bases 21126–22379, 22692–23669, 23793–24041, 24102–25349, 25683–26684, 27582–28121, and 28404–28649 of SEQ ID NO:1.

In another of its aspects, the invention provides an isolated DNA molecule comprising a DNA sequence that encodes a spinosyn PKS domain selected from KS2, AT2, DH2, ER2, KR2, and ACP2, said domains being described by, respectively, amino acids 1–424, 536–866, 892–1077, 1338–1683, 1687–1866, and 1955–2034 of SEQ ID NO:3. In a preferred embodiment the DNA sequence is selected from the group consisting of bases 29024–30295, 30629–31621, 31697–32254, 33035–34072, 34082–34621, 34886–35125 of SEQ ID NO:1.

In another of its aspects, the invention provides an isolated DNA molecule comprising a DNA sequence that encodes a spinosyn PKS domain selected from KS3, AT3, KR3, ACP3, KS4, AT4, KR4, and ACP4, said domains being described by, respectively, amino acids 1–423, 531–280, 1159–1337, 1425–1506, 1529–1952, 2066–2396, 2700–2880, and 2972–3053 of SEQ ID NO:4. In a preferred embodiment the DNA sequence is selected from the group consisting of bases 35518–36786, 37108–38097, 38992–39528, 39790–40035, 40102–41373, 41713–42705, 43615–44157, and 44431–44676 of SEQ ID NO: 1.

In another of its aspects the invention provides an isolated DNA molecule comprising a DNA sequence that encodes a spinosyn PKS domain selected from KS5, AT5, DH5, KR5, ACP5, KS6, AT6, KR6, ACP6, KS7, AT7, KR7, and ACP7, said domains being described by, respectively, amino acids 1–424, 539–866, 893–1078, 1384–1565, 1645–1726, 1748–2172, 2283–2613, 2916–3095, 3188–3269, 3291–3713, 3825–4153, 4344–4638, and 4725–4806 of SEQ ID NO:5. In a preferred embodiment the DNA sequence is selected from the group consisting of bases 45077–46348, 46691–47674, 47753–48310, 49226–49771, 50009–50254, 50318–51592, 51923–52915, 53822–54361, 54638–54883, 54947–56215, 56549–57535, 58106–58990, and 59249–59494 of SEQ ID NO:1.

In another of its aspects, the invention provides an isolated DNA molecule comprising a DNA sequence that encodes a spinosyn PKS domain selected from KS8, AT8, DH8, KR8, ACP8, KS9, AT9, DH9, KR9, ACP9, KS10, AT10, DH10, KR10, ACP10, and TE10, said domains being described by, respectively, amino acids 1–424, 530–848, 883–1070, 1369–1552, 1648–1726, 1749–2173, 2287–2614, 2640–2800, 3157–3341, 3422–3500, 3534–3948, 4060–4390, 4413–4597, 4900–5078, 5172–5253, and 5302–5555 of SEQ ID NO:6. In a preferred embodiment, the DNA sequence is selected from the group consisting of bases 59902–61173, 61489–62445, 62548–63111, 64006–64557, 64843–65079, 65146–66420, 66760–67743, 67819–68301, 69370–69924, 70165–70401, 70471–71745, 72079–73071, 73138–73692, 74599–75135, 75415–75660, and 75805–76566 of SEQ ID NO: 1.

In another of its aspects the invention provides an isolated DNA molecule comprising a DNA sequence that encodes a spinosyn PKS module, said module being selected from the group consisting of amino acids 6–1413 of SEQ ID NO:2, 1525–2513 of SEQ ID NO:2, 1–2034 of SEQ ID NO:3, 1–1506 of SEQ ID NO:4, 1529–3053 of SEQ ID NO:4, 1–1726 of SEQ ID NO:5, 1748–3269 of SEQ ID NO:5, 3291–4806 of SEQ ID NO:5, 1–1726 of SEQ ID NO:5, 1–1726 of SEQ ID NO:6, 1749–3500 of SEQ ID NO:6, and 35434–5555 of SEQ ID NO:6. In a preferred embodiment the DNA sequence is selected from the group consisting of bases 21126–24041, 24102–28649, 29024–35125, 35518–40035, 40102–44676, 45077–50254, 50318–54883, 54947–59494, 59902–65079, 65146–70401, and 70471–76566 of SEQ ID NO:1.

In another of its aspects, the invention provides a recombinant DNA vector which comprises a DNA sequence of the invention as described above.

In another of its aspects the invention provides a host cell transformed with a recombinant vector of the invention as described above.

In another of its aspects, the invention provides a method of increasing the spinosyn-producing ability of a spinosyn-producing microorganism comprising the steps of 1) transforming with a recombinant DNA vector or portion thereof a microorganism that produces spinosyn or a spinosyn precursor by means of a biosynthetic pathway, said vector or portion thereof comprising a DNA sequence of the invention, as described above, that codes for the expression of an activity that is rate limiting in said pathway, and 2) culturing said microorganism transformed with said vector under conditions suitable for cell growth and division, expression of said DNA sequence, and production of spinosyn.

In another of its aspects the invention provides a spinosyn-producing microorganism having operative spinosyn biosynthetic genes wherein at least one of the spinosyn biosynthetic genes spnA, spnB, spnC, spnD, spnE, spnF, spnG, spnH, spnI, spnJ, spnK, spnL, spnM, spnN, spnO, spnP, spnQ, spnR, spnS, *S. spinosa* gtt, *S. spinosa* gdh, *S. spinosa* epi, or *S. spinosa* kre has been duplicated.

In another of its aspects the invention provides a spinosyn-producing microorganism, said microorganism having spinosyn biosynthetic genes in its genome, wherein at least one of said genes has been disrupted by recombination with an internal fragment of that gene, the rest of said genes being operational to produce a spinosyn other than the one that would be produced if the disrupted gene were operational. Preferably the microorganism is an *S. spinosa* mutant.

The invention also provides a spinosyn-producing microorganism having operational spinosyn biosynthetic genes in its genome, wherein said genes a) include at least one operational PKS module more than or at least one less than is present in SEQ ID NO:1; or b) include a PKS module that differs from the corresponding module described in SEQ ID NO:1 by the deletion, inactivation, or addition of a KR, DH or ER domain, or by the substitution of an AT domain. Preferably the microorganism is an *S. spinosa* mutant.

The invention also provides spinosyns produced by cultivation of the novel microorganisms of the invention.

In another of its aspects the invention provides a process for isolating spinosyn biosynthetic genes which comprises creating a genomic library of a spinosyn producing microorganism, and using a labeled fragment of SEQ ID NO: 1 that is at least 20 bases long as a hybridization probe.

DETAILED DESCRIPTION OF THE INVENTION

Figure 3:
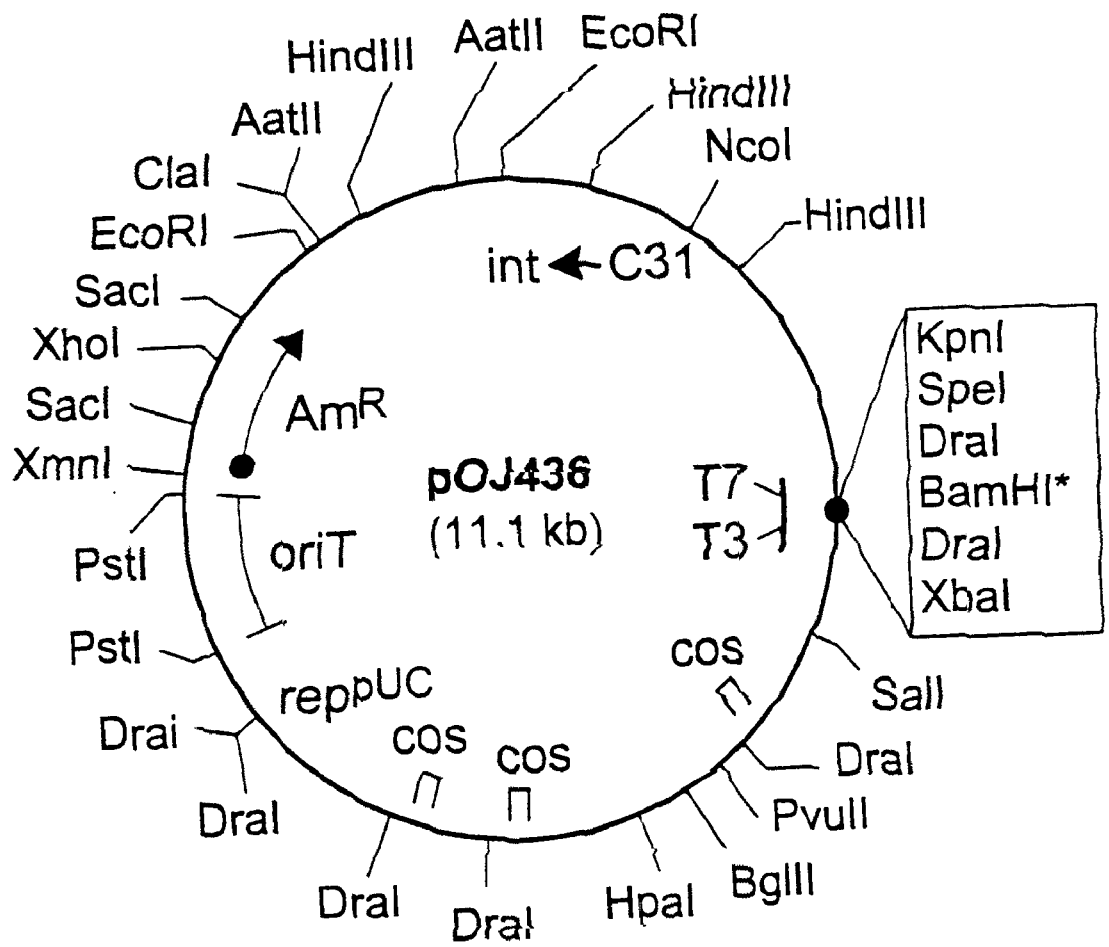
FIG. 3 is a restriction site and functional map of Cosmid pOJ436.
Figure 4:
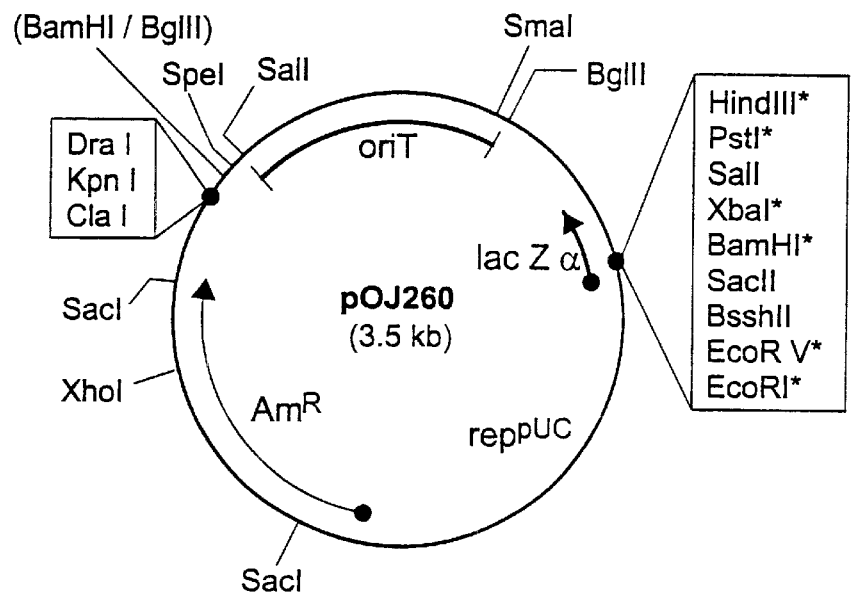
FIG. 4 is a restriction site and functional map of Cosmid pOJ260.

A cosmid library of *S. spinosa* (NRRL 18395) DNA was constructed from fragments generated by partial digestion with Sau3A I. They were cloned into the BamHI site of vector pOJ436 (See FIG. 3) (Bierman et al., 1992) and introduced into E. coli cells by in vitro packaging and transduction. The library of recombinant bacteria thus prepared was screened for homology to two radiolabelled DNA probes by hybridization using the methods of Solenberg & Burgett (1989). One probe was the 400 kb SpeI fragment which is often deleted in non-producing S. spinosa strains generated by transformation or mutagenesis with N-methyl-N'-nitro-N-nitrosoguanidine (Matsushima et al., 1994). The second probe was a 300 bp piece of S. spinosa DNA that codes for part of a ketosynthase not involved in spinosyn biosynthesis (B. E. Schoner, personal communication). It includes a region which is highly conserved in all polyketide and fatty acid synthase genes, and was therefore expected to cross-hybridize with the spinosyn PKS genes. Cosmids 9A6 and 2C10 were two of seven clones that hybridized to both probes. Cosmid 3E11 was selected from the genomic library by hybridization to a radiolabelled SgrA1-BamH1 fragment of cosmid 9A6 (bases 26757–26936 in SEQ ID NO: 1). To determine the nucleotide sequence of the insert in cosmid 9A6, BamHI fragments were subcloned into the BamHI site of plasmid pOJ260 (See FIG. 4) (Bierman et al., 1992). The sequences of the inserts in these plasmids were determined by either of two methods. In one method, subcloned fragments were partially digested with Sau3A I, and size-selected pieces were cloned into the BamHI site of DNA from the phage M13mp19. Single-stranded DNA was prepared from randomly selected recombinants, and sequenced by fluorescent cycle sequencing using reagents and equipment from ABI (Applied Biosystems, Inc., Foster, Calif.), according to the methods of Burgett & Rosteck (1994). The sequences from phage subclones of each plasmid were assembled into one contiguous sequence. In the other sequencing method, double-stranded plasmid DNAs were primed reiteratively with single-stranded oligonucleotides, each designed to complement a region near the end of previously determined sequence. The complete sequence was thus compiled from a series of partially-overlapping sequences. Prism-Ready Sequencing Kits (ABI) were used according to the manufacturer's instructions, and analyzed on an ABI373A Sequencer. The same strategy was employed to sequence across the BamHI sites of double-stranded 9A6 DNA. These data allowed the subcloned sequences to be aligned and oriented relative to one another using the AssemblyLIGN module of the MacVector program (Oxford Molecular, Campbell, Ky.), and thereby allowed the entire nucleotide sequence of the S. spinosa DNA in cosmid 9A6 to be assembled. The complete sequences of cosmids 2C10 and 3E11 were determined by the method of fluorescent cycle sequencing of random DNA fragments cloned in phage M13 (SeqWright, Houston, Tex.). The inserts in cosmids 2C10 and 3E11 overlapped, and the insert in 3E11 overlapped the end of the insert in cosmid 9A6. See FIG. 2. Together, the three cosmid inserts spanned about 80 kb of unique sequence (SEQ ID NO: 1). The following Table 3 identifies the portions of SEQ ID NO:1 included in each of the three inserts.

TABLE 3

| insert | bases in SEQ ID NO:1 |
|---|---|
| cosmid 9A6 | 1–26941 |
| cosmid 3E11 | 23489–57287 |
| cosmid 2C10 (corrected) | 41429–80161 |

Figure 2:
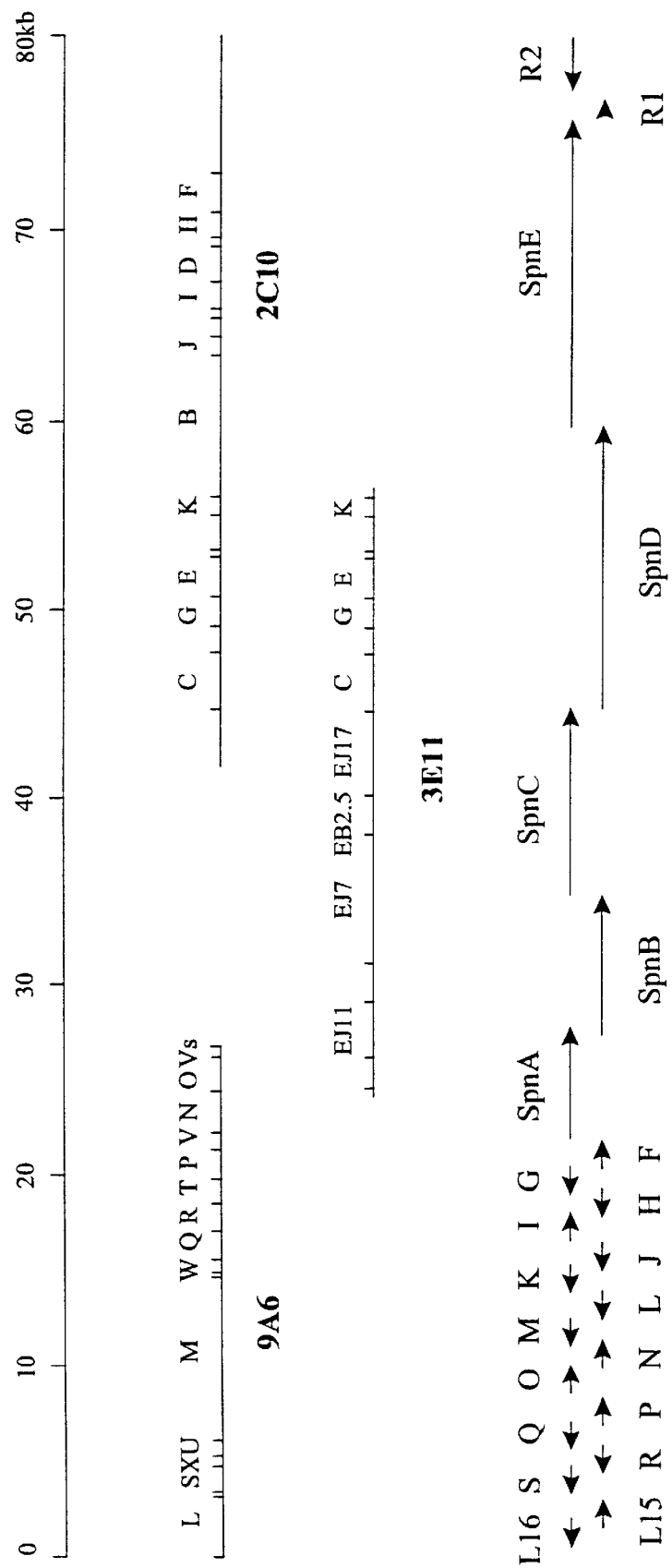
FIG. 2 is a map illustrating the arrangement of BamHI fragments and open reading frames in the cloned region of *S. spinosa* DNA.

FIG. 2 gives a graphical representation of the relationship of the three inserts to the 80 kb of sequence.

It should be noted that cosmid 2C10 was missing bases G41877, C45570, C57845 and G73173 of SEQ ID NO:1. These deletions were determined to be cloning artifacts. The deletions generated in-frame stop codons that truncated PKS polypeptides. One of them occurred in a region also cloned in cosmid 3E11, but was not present in the region of 3E11 for which sequence was obtained. Uncloned DNA spanning all 8 stop codons in the PKS region was therefore sequenced directly from PCR-amplified regions of the genome of S. spinosa (NRRL 18395). The sequences from uncloned DNA confirmed the existence of the 4 stop codons at the end of ACP domains, and proved that the 4 frameshifts within other coding regions were cloning artifacts unique to cosmid 2C10.

PKS Genes

SEQ ID NO:1 includes a central region of about 55 kb with striking homology to the DNA encoding the polyketide synthases of known macrolide producers (Donadio et al., 1991; MacNeil et al., 1992; Schwecke et al., 1995; Dehoff et al., 1997). The spinosyn PKS DNA region consists of 5 ORFs with in-frame stop codons at the end of ACP domains, similar to the PKS ORFs in the other macrolide-producing bacteria. The five spinosyn PKS genes are arranged head-to-tail (see FIG. 2), without any intervening non-PKS functions such as the insertion element found between the erythromycin PKS genes AI and AII (Donadio et al., 1993). They are designated spnA, spnB, spnC, spnD, and spnE. The nucleotide sequence for each of the five spinosyn PKS genes, and the corresponding polypeptides, are identified in the following Table 4:

TABLE 4

| GENE | BASES IN SEQ ID NO:1 | CORRESPONDING POLYPEPTIDE |
|---|---|---|
| spnA | 21111–28898 | SEQ ID NO: 2 |
| spnB | 28916–35374 | SEQ ID NO: 3 |
| spnC | 35419–44931 | SEQ ID NO: 4 |
| spnD | 44966–59752 | SEQ ID NO: 5 |
| spnE | 59803–76569 | SEQ ID NO: 6 | spnA encodes the initiator module (SEQ ID NO:1, bases 21126–24041) and extender module 1 (SEQ ID NO:1, bases 24102–28649). The nucleotide sequence and corresponding amino acid sequence for each of the functional domains within the initiator module and extender module 1 are identified in the following Table 5:

TABLE 5

| spnA | | |
|---|---|---|
| DOMAIN | BASES IN SEQ ID NO:1 | AMINO ACIDS IN SEQ ID NO:2 |
| KSi | 21126–22379 | 6–423 |
| ATi | 22692–23669 | 528–853 |
| ACPi | 23793–24041 | 895–977 |
| KS1 | 24102–25349 | 998–1413 |
| AT1 | 25683–26684 | 1525–1858 |
| KR1 | 27582–28121 | 2158–2337 |
| ACP1 | 28404–28649 | 2432–2513 | spnB encodes extender module 2 (SEQ ID NO:1, bases 29024–35125). The nucleotide sequence and corresponding amino acid sequence for each of the functional domains within extender module 2 are identified in the following Table 6:

TABLE 6 spnB

| DOMAIN | BASES IN SEQ ID NO:1 | AMINO ACIDS IN SEQUENCE ID NO. 3 |
|---|---|---|
| KS2 | 29024–30295 | 1–424 |
| AT2 | 30629–31621 | 536–866 |
| DH2 | 31697–32254 | 892–1077 |
| ER2 | 33035–34072 | 1338–1683 |
| KR2 | 34082–34621 | 1687–1866 |
| ACP2 | 34886–35125 | 1955–2034 | spnC encodes extender module 3 (SEQ ID NO:1, bases 35518–40035) and extender module 4 (SEQ ID NO:1, bases 40102–44676). The nucleotide sequence and corresponding amino acid sequence for each of the functional domains within extender modules 3 and 4 are identified in the following Table 7:

TABLE 7 spnC

| DOMAIN | BASES IN SEQ ID NO:1 | AMINO ACIDS IN SEQ ID NO:4 |
|---|---|---|
| KS3 | 35518–36786 | 1–423 |
| AT3 | 37108–38097 | 531–280 |
| KR3 | 38992–39528 | 1159–1337 |
| ACP3 | 39790–40035 | 1425–1506 |
| KS4 | 40102–41373 | 1529–1952 |
| AT4 | 41713–42705 | 2066–2396 |
| KR4 | 43615–44157 | 2700–2880 |
| ACP4 | 44431–44676 | 2972–3053 | spnD encodes extender module 5 (SEQ ID NO:1, bases 45077–50254), extender module 6 (SEQ ID NO:1, bases 50318–54883), and extender module 7 (SEQ ID NO:1, bases 54947–59494). The nucleotide sequence and corresponding amino acid sequence for each of the functional domains within extender modules 5, 6, and 7 is identified in the following Table 8:

TABLE 8 spnD

| DOMAIN | BASES IN SEQ ID NO:1 | AMINO ACIDS IN SEQ ID NO:5 |
|---|---|---|
| KS5 | 45077–46348 | 1–424 |
| AT5 | 46691–47674 | 539–866 |
| DH5 | 47753–48310 | 893–1078 |
| KR5 | 49226–49771 | 1384–1565 |
| ACP5 | 50009–50254 | 1645–1726 |
| KS6 | 50318–51592 | 1748–2172 |
| AT6 | 51923–52915 | 2283–2613 |
| KR6 | 53822–54361 | 2916–3095 |
| ACP6 | 54638–54883 | 3188–3269 |
| KS7 | 54947–56215 | 3291–3713 |
| AT7 | 56549–57535 | 3825–4153 |
| KR7 | 58106–58990 | 4344–4638 |
| ACP7 | 59249–59494 | 4725–4806 | spnE encodes extender module 8 (SEQ ID NO:1, bases 59902–65079), extender module 9 (SEQ ID NO:1, bases 65146–70401), and extender module 10 (SEQ ID NO:1, bases 70471–76566). The nucleotide sequence and corresponding amino acid sequence for each of the functional domains within extender modules 8, 9, and 10 is identified in the following Table 9:

TABLE 9 spnE

| DOMAIN | BASES IN SEQ ID NO:1 | AMINO ACIDS IN SEQ ID NO:6 |
|---|---|---|
| KS8 | 59902–61173 | 1–424 |
| AT8 | 61489–62445 | 530–848 |
| DH8 | 62548–63111 | 883–1070 |
| KR8 | 64006–64557 | 1369–1552 |
| ACP8 | 64843–65079 | 1648–1726 |
| KS9 | 65146–66420 | 1749–2173 |
| AT9 | 66760–67743 | 2287–2614 |
| DH9 | 67819–68301 | 2640–2800 |
| KR9 | 69370–69924 | 3157–3341 |
| ACP9 | 70165–70401 | 3422–3500 |
| KS10 | 70471–71745 | 3534–3948 |
| AT10 | 72079–73071 | 4060–4390 |
| DH10 | 73138–73692 | 4413–4597 |
| KR10 | 74599–75135 | 4900–5078 |
| ACP10 | 75415–75660 | 5172–5253 |
| TE10 | 75805–76566 | 5302–5555 |

The boundaries and functions of the 50 domains identified in the foregoing Tables 5–9 are predicted based on similarities to the conserved amino acid sequences of the domains in other polyketide synthases, particularly the erythromycin polyketide synthase (Donadio et al., 1992). The unexpected KSi domain at the amino terminus of the initiator module is presumed to be non-functional because it contains a glutamine residue at amino acid 172, in place of the cysteine required for β-ketosynthase activity (Siggard-Andersen, 1993). A similar non-functional KS domain has been discovered in the initiator module of the tylosin PKS (Dehoffet al., 1997). The other spinosyn PKS domains are functional. None of them has the sequence characteristics of the inactive domains found in the erythromycin and rapamycin PKS genes (Donadio et al., 1991; Aparicio et al., 1996). The cloned PKS genes were shown to be essential for spinosyn biosynthesis by the discovery that strains of S. spinosa in which these genes had been disrupted were unable to produce spinosyns by fermentation. Gene disruption was achieved by cloning an internal fragment of the gene into plasmid pOJ260 (FIG. 4), using procedures well-known to those skilled in the art. The recombinant plasmids were then introduced into S. spinosa by conjugation from E. coli using the procedures of Matsushima et al. (1994), and selecting for apramycin-resistant exconjugants. Plasmids based on pOJ260 do not replicate independently in S. spinosa, and are stably maintained by integrating the plasmid into the chromosome via recombination between the cloned DNA and its homologous sequence in the genome. Integration creates two incomplete versions of the targeted gene (one lacking 5' sequences and one lacking 3' sequences) in the chromosome, with the pOJ260 DNA between them. Spinosyn biosynthesis was blocked by disrupting the spnA ORF with the BamH1 fragments V, N, or K, corresponding respectively to the following segments of SEQ ID NO: 1: 21365–22052, 22052–24338, or 24338–26227. Spinosyn biosynthesis was also blocked by disrupting the spnD ORF with BamH1 fragments G, E, or K, corresponding respectively to the following segments of SEQ ID NO: 1: bases 48848–50578, 50578–52467, or 55207–55888. Spinosyn biosynthesis was also blocked by disrupting the spnE ORF with BamH1 fragments J, I, D, H, and F, corresponding respectively to the following segments of SEQ ID NO: 1: 63219–63989, 65406–66733, 66733–68997, 69369–70731, and 70731–72675. Spinosyn biosynthesis was not blocked by integration via BamH1 fragments C (bases 44612–47565 in SEQ ID NO: 1) or B (bases 55936–63219 in SEQ ID NO: 1) because they are not internal to any one gene; BamH1 fragment C spans the junction between spnC and spnD, and BamH1 fragment B spans the junction between spnD and spnE. In these cases, integration leaves one complete version of each gene.

Genes Adjacent to the PKS Responsible for Additional Modifications

In the DNA upstream of the PKS genes (cloned in cosmid 9A6) there were 16 open reading frames (ORFs), each consisting of at least 100 codons, beginning with ATG or GTG and ending with TAA, TAG or TGA, and having the codon bias expected of protein-coding regions in an organism whose DNA contains a high percentage of guanine and cytosine residues (Bibb et al., 1984). See the bottom right hand side of FIG. 2 for a graphical representation of the 16 ORFs in 9A6. Based on evidence that will be discussed hereinafter, 14 of the ORFs have been designated as spinosyn biosynthetic genes, namely: spnF, spnG, spnH, spnI, spnJ, spnK, spnL, spnM, spnN, spnO, spnP, spnQ, spnR, and spnS (they are labeled F through S in FIG. 2). In the following Table 10, the DNA sequence and the amino acid sequence for the corresponding polypeptide are identified for each of these genes, as well as for two ORFs (ORFL15 and ORFL16) found immediately upstream of spnS. Also identified in Table 10 are the nucleotide sequences for ORFR1 and ORFR2 downstream of the PKS genes (in cosmid 2C10), and the amino acid sequences corresponding to them.

TABLE 10

| GENE | BASES IN SEQUENCE ID NO: 1 | POLYPEPTIDE |
| --- | --- | --- |
| spnF | 20168–20995 | SEQ ID NO: 7 |
| spnG | 18541–19713 (C) | SEQ ID NO: 8 |
| spnH | 17749–18501 (C) | SEQ ID NO: 9 |
| spnI | 16556–17743 | SEQ ID NO: 10 |
| spnJ | 14799–16418 (C) | SEQ ID NO: 11 |
| spnK | 13592–14785 (C) | SEQ ID NO: 12 |
| spnL | 12696–13547 (C) | SEQ ID NO: 13 |
| spnM | 11530–12492 (C) | SEQ ID NO: 14 |
| spnN | 10436–11434 | SEQ ID NO: 15 |
| spnO | 8967–10427 | SEQ ID NO: 16 |
| spnP | 7083–8450 | SEQ ID NO: 17 |
| spnQ | 5363–6751 (C) | SEQ ID NO: 18 |
| spnR | 4168–5325 (C) | SEQ ID NO: 19 |
| spnS | 3416–4165 (C) | SEQ ID NO: 20 |
| ORFL 15 | 2024–2791 | SEQ ID NO: 21 |
| ORFL 16 | 1135–1971 (C) | SEQ ID NO: 22 |
| ORFR 1 | 76932–77528 | SEQ ID NO: 23 |
| ORFR 2 | 77729–79984 | SEQ ID NO: 24 |

(C) indicates complementary strand is given in the sequence listing

To assign functions to the polypeptides identified in Table 10, three lines of evidence were utilized: similarity to sequences of known function, results of targeted gene disruption experiments, and results of bioconversion experiments.

The amino acid sequences of the predicted polypeptides were compared to sequences deposited in the databases at the National Center for Biotechnology Information (NCBI, Washington, D.C.), using the BLAST algorithm to determine how well they are related to known proteins. The BLAST searches of the NCBI databases were also repeated periodically to obtain new insights from additional homologies. Table 11 gives the best matches from a basic BLAST search on Jan. 12, 1998:

TABLE 11

| Gene | Significant Protein Match | GenBank Accession | BLAST Score* | Reported function |
| --- | --- | --- | --- | --- |
| spnF | C-24 sterol methyl-transferase (*Zea mays*) | U79669 | 202 | C-methylation |
| spnG | Daunosamyl transferase dnrS (*Streptomyces peucetius*) | L47164 | 202 | sugar addition |
| spnH | Mycinamicin III O-methyltransferase (*Micromonospora griseorubida*) | D16097 | 408 | sugar methylation |
| spnI | ORFY (*Streptomyces nogalater*) | Z48262 | 192 | unknown |
| spnJ | Hexose oxidase (*Chondrus crispus*) | U89770 | 143 | oxido-reduction |
| spnK | ORFY (*Streptomyces nogalater*) | Z48262 | 137 | unknown |

In targeted gene disruptions, internal fragments were generated by PCR amplification from the cosmid DNAs, and cloned into plasmid pOJ260. The resulting plasmids were then conjugated into *S. spinosa* (NRRL 18395), and apramycin-resistant exconjugants were isolated and fermented. As stated earlier, the basis of disruption experiments is that when a plasmid bearing an internal gene fragment is integrated, two incomplete copies of the biosynthetic gene result, thereby eliminating the enzymatic function. Resulting fermentation products were analyzed to determine which spinosyns accumulated. The results of the targeted gene disruption experiments are summarized in Table 12.

In bioconversion studies, strains in which spinosyn synthesis was altered were tested for their ability to convert available spinosyn intermediates to other spinosyns. The intermediates used were spinosyn A Aglycone (AGL), spinosyn P (P), spinosyn K (K), and spinosyn A 9-Psa (PSA). The results of the bioconversion experiments are also summarized in Table 12

TABLE 12

| Disrupted Gene | Internal Fragment in SEQ ID NO: 1 | spinosyns accumu-lated | Bioconversion products | | | |
| --- | --- | --- | --- | --- | --- | --- |
| | | | AGL→ | P→ | K→ | PSA→ |
| None | None | A + D | | | | |
| spnF | 20325–20924 | None | A | A | | A |
| spnG | 18818–19426 | None | AGL | K | | A |
| spnG–H | 18511–19559 | P | | | K | A |
| spnI | 16699–17400 | None | | J | A | A |
| spnJ | 14866–15470 | None | A | | A | |
| spnK | 13785–14574 | None | | | | |
| spnL | 12791–13428 | None | A | A | | A |
| spnM | 11705–12371 | 3% A | A | | | A |
| spnN | 10636–11369 | PSA | | | | |
| spnO | 9262–10226 | PSA | | | | |
| spnP | 7391–8159 | PSA | PSA | | | |
| ORFL15 | 2145–2719 | A + D | | | | |
| ORFL16 | 1226–1852 | A + D | | | | |
| ORFR2 | 79321–79855 | A + D | | | | |

The conclusions drawn from BLAST searches, the gene disruption experiments, and the bioconversion studies will now be discussed in greater detail on a gene by gene basis.

The 11 genes upstream of the PKS were shown to be involved in spinosyn biosynthesis because strains in which they were disrupted failed to accumulate the major spinosyns A and D (Table 12). The next 2 genes upstream (ORFL15, ORFL16), and the large gene downstream (ORFR2) of the PKS, do not contribute to spinosyn production because fermentation was not affected by their disruption (Table 12). Disruption of the ORF immediately downstream of the PKS genes (ORFR1) was not attempted because it was too small to yield an internal fragment that would recombine at an acceptable frequency. Disruptions of the spnQ, spnR, and spnS genes were not attempted because early BLAST searches showed that these genes had striking similarity to enzymes known to be involved in the biosynthesis of unusual deoxysugars. spnQ had 53% identity between its gene product and the CDP-4-keto-6-deoxy-D-glucose-3-dehydrase involved in synthesis of the abequose moiety of the *Salmonella enterica* cell surface lipopolysaccharide (Jiang et al., 1991); spnR had up to 40% identity between its product and a group of proteins proposed to function as deoxysugar transaminases (Thorson et al., 1993); and spnS had 42% identity between its product and the SrmX product of *Streptomyces ambofaciens*, an organism that synthesizes the forosamine-containing antibiotic spiramycin (Geistlich et al., 1992). Even stronger similarities have emerged from recent BLAST searches (Table 11). Based on these similarities, and the close linkage of the genes to other spinosyn biosynthetic genes, it is concluded that spnQ, spnR, and spnS are involved in production of the forosamine moiety of spinosyns. spnF, spnJ, spnL, spnM Strains disrupted in genes spnF, spnJ, spnL or spnM did not accumulate any spinosyns to significant levels (the low level of spinosyn A in the spnM mutant presumably resulted from some residual activity in the gene product deleted at its carboxy terminus). However, they bioconverted exogenously-supplied aglycone to spinosyn A, and therefore contained all the enzymes necessary for the later steps in spinosyn biosynthesis. These particular genes must be involved in generation of the aglycone from the putative monocyclic lactone product of the PKS genes. Roles for spnF and spnL in the formation of carbon-carbon bridges are consistent with their similarities to enzymes that methylate carbon atoms (Table 11). The absence of partially modified intermediates in the blocked mutants may result from instability of the compounds, or from reduced biosynthesis due to lack of glycosylated molecules to act as positive regulators, analogous to those of the tylosin pathway (Fish & Cundliffe, 1997). spnG, spnH, spnI, spnK Disruption of spnG also prevented spinosyn production, but the mutant strain could not bioconvert aglycone so this gene is required for a later step in the pathway (Table 12). Its sequence similarity to known glycosyl transferase genes (Table 11) suggests that spnG encodes the rhamnosyl transferase required for addition of the first sugar to the aglycone. The mutant with a disrupted spnG also lacked a functional 4'-O-methyltransferase (OMT) because it converted the 3',4'-didesmethyl spinosyn (P) to the 4'-desmethyl spinosyn (K), but not to the fully methylated spinosyn A. The 4'-OMT activity was presumably not expressed in the mutant because the encoding gene (spnH) lies downstream of the disrupting integration in the same operon. The existence of this operon was confirmed by disrupting BamH1 fragment T, which spans the junction between spnG and spnH but is not internal to any open reading frame. Nevertheless, its disruption altered spinosyn synthesis, so this fragment must be internal to a single transcript that encompasses both genes. In addition to the expected loss of 4'-OMT activity encoded by spnH, this disruption also caused the unexpected loss of 3'-OMT function, leading to accumulation of spinosyn P (Table 12). The 3'OMT activity appears to be encoded by the convergent downstream gene, spnI. This gene has most sequence similarity to the ORF Y gene of *Streptomyces nogalator* (Table 11). The function of the ORF Y product is unknown, but the organism produces an unusual tetramethylated deoxysugar (nogalose) that is similar to the tri-methylated rhamnose of spinosyn A, so presumably both genes are involved in sugar methylation. Consistent with this hypothesis, disruption of spnI created a mutant that bioconverted spinosyn P only to the 3'-desmethyl spinosyn (J), not spinosyn A (Table 12). The disruption prevented any spinosyn accumulation in unsupplemented fermentations. spnK has a sequence similar to spnI and ORF Y, and presumably encodes the 2'-OMT. Its disruption also prevented accumulation of any spinosyns in unsupplemented fermentations (Table 12). spnN, spnO, spnP.

Disruption of genes spnN, spnO and spnP led to accumulation of the pseudoaglycone (Table 12). These genes are therefore involved in the biosynthesis or addition of the forosamine sugar. The similarity of spnP to glycosyl transferases (Table 11) indicates that it encodes the spinosyn forosamyl transferase. The high degree of similarity between spnO and a 2,3 dehydratase (Table 11) indicates that it is involved in the 2'-deoxygenation step of forosamine synthesis.

Rhamnose Genes

The overlapping inserts cloned in cosmids 9A6, 3E11 and 2C10 do not contain genes that encode the four enzymes required to produce rhamnose from glucose (Liu & Thorson, 1994). The first enzyme is a glucose thymidylate transferase (gtt), or equivalent enzyme, that activates glucose by addition of a nucleotidyl diphosphate (NDP). The second is a glucose dehydratase (gdh) to produce NDP-4-keto-6-deoxy-glucose, an intermediate common to many deoxysugar biosynthetic pathways. An epimerase (epi) and a ketoreductase (kre) specific for rhamnose synthesis are also required, to convert the NDP-4-keto-6-deoxy-glucose to NDP-L-rhamnose, the activated sugar that is the substrate of the glycosyltransferase adding rhamnose to the aglycone. Genes that code for these enzymes in *S. spinosa* were cloned from a separate library of 7–12 kb partial Sau3AI fragments in the λ vector ZAP Express™ (Stratagene, LaJolla, Calif.). Radio-labelled probes were prepared by random primer extension (Boehringer Mannheim, Indianapolis, Ind.) of fragments from plasmid pESC1 containing the *Saccharopolyspora erythraea* gdh (Linton et al., 1995) and gtt genes. Plaque hybridizations to screen the phage library were performed with a stringent wash of 0.5×SSC, 0.1%SDS at 65° C. for 1 h. The plasmid (pDAB1620 and pDAB1621) portions of the vector containing inserts were excised from two of the three hybridizing phage, and partially sequenced using Prism-Ready Sequencing Kits (ABI) and multiple primers. The sequenced part of the insert in pDAB1620 (SEQ ID NO: 25) includes an ORF that would encode a 329-amino acid polypeptide (SEQ ID NO:26) with 82% identity to the gdh product of *S. erythraea*. Adjacent to this gene is an ORF coding for a 275-amino acid polypeptide (SEQ ID NO:27) with 72% identity to the *S. erythraea* kre gene product. The sequenced part of the insert in pDAB1621 (SEQ ID NO: 28) contains an ORF encoding a 261-amino acid polypeptide (SEQ ID NO: 29) with 83% identity to the *S. erythraea* gtt gene product. A second probe for rhamnose genes was prepared by PCR amplification of *S. spinosa* genomic DNA using degenerate oligonucleotide primers (SEQ ID NO: 30 and SEQ ID NO: 31) based on conserved amino acid regions in known epi proteins (Jiang et al., 1991; Linton et al., 1995). PCR reactions were performed in a GeneAmp 9600 Thermocycler with AmpliTaq polymerase (Perkin-Elmer) using 30 cycles of 30 sec at 94° C., 30 sec at 60° C. and 45 sec at 72° C. The probe hybridized to one phage in the 7–12 kb library; the plasmid portion of the vector containing this insert (pDAB 1622) was excised and partially sequenced (SEQ ID NO:32). It includes an ORF for a 202-amino acid polypeptide (SEQ ID NO:33) with 57% homology to the *S. erythraea* epi protein. The genes were disrupted by recombination with plasmids containing internal fragments (bases 382–941 in SEQ ID NO: 25, 1268–1867 in SEQ ID NO:25, 447–994 in SEQ ID NO:28 or 346–739 in SEQ ID NO:32). Apramycin-resistant exconjugants were obtained in all cases, but they were only capable of growth on osmotically-stabilized media such as CSM supplemented with sucrose at 200 g/L, or R6 (Matsushima et al., 1994). Even under these conditions, they grew much slower than the parent *S. spinosa* (NRRL 18395), and were morphologically distinct, with highly fragmented mycelia. These results could be due to the presence of rhamnose in the cell wall in *S. spinosa* and a requirement that these four genes be present for normal cell wall synthesis in this organism. Mutants disrupted in these genes grew too slowly to be fermented under conditions known to produce spinosyns. However, Southern hybridizations of *S. spinosa* genomic DNA with the *S. erythraea* gtt/gdh probe (washed in 2×SSC, 0.%SDS at 65° C. for 1 h) or with the degenerate epi probe (washed in 0.1×SSC, 0.1%SDS at 65° C. for 1 h) indicated that there are no other homologues of these genes present in the *S. spinosa* genome. Therefore, the four cloned *S. spinosa* genes must be the sole source of rhamnose for both cell wall formation and spinosyn biosynthesis.

The nucleotide sequence and corresponding amino acid sequence for each of the four *S. spinosa* genes required to produce rhamnose are identified in the following Table 13:

TABLE 13

| gene | DNA sequence | amino acid sequence |
| --- | --- | --- |
| S. spinosa gtt | SEQ ID NO:28, bases 334–1119 | SEQ ID NO:29 |
| S. spinosa gdh | SEQ ID NO:25, bases 88–1077 | SEQ ID NO:26 |
| S. spinosa epi | SEQ ID NO:32, bases 226–834 | SEQ ID NO:33 |
| S. spinosa kre | SEQ ID NO:25, bases 1165–1992 | SEQ ID NO:27 |

Thus 23 genes from *S. spinosa* can be assigned roles in spinosyn biosynthesis: 5 PKS genes to produce a macrocyclic lactone, 4 genes to modify this to the aglycone, 5 genes to synthesize and add rhamnose, 3 genes to methylate the rhamnose, and 6 genes to synthesize and add forosamine. The hypothetical biosynthetic pathway is summarized in FIG. 1.

Utility

There are many uses for the cloned *Saccharopolyspora spinosa* DNA. The cloned genes can be used to improve yields of spinosyns and to produce new spinosyns. Improved yields can be obtained by integrating into the genome of a particular strain a duplicate copy of the gene for whatever enzyme is rate limiting in that strain. In the extreme case where the biosynthetic pathway is blocked in a particular mutant strain due to lack of a required enzyme, production of the desired spinosyns can be restored by integrating a copy of the required gene. Yield improvement obtained by integrating copies of spinosyn genes is illustrated hereinafter in Examples 1–3 and 6.

Novel spinosyns can be produced using fragments of the cloned DNA to disrupt steps in the biosynthesis of spinosyns. Such disruption may lead to the accumulation of precursors or "shunt" products (the naturally-processed derivatives of precursors). The fragments useful in carrying out disruptions are those internal to a gene with bases omitted from both the 5' and 3' ends of the gene. Homologous recombination events utilizing such fragments result in two partial copies of the gene: one that is missing the omitted bases from the 5' end and one that is missing the omitted bases from the 3' end. The number of bases omitted at each end of the fragment must be large enough so that neither of the partial copies of the gene retains activity. At least 50 bases will normally be omitted from each end, and more preferably at least 100 bases are omitted from each end. The length of the partial gene fragment should be large enough so that recombination frequency is high enough for a practical experiment. Useful fragments for disruptions are desirably at least 300 bases long, and more preferably at least about 600 bases long. Modified spinosyns produced by disrupting genes may be insect control agents themselves, or serve as substrates for further chemical modification, creating new semi-synthetic spinosyns with unique properties and spectra of activity. Example 4 hereinafter illustrates the use of disruption.

Novel spinosyns can also be produced by mutagenesis of the cloned genes, and substitution of the mutated genes for their unmutated counterparts in a spinosyn-producing organism. Mutagenesis may involve, for example: 1) deletion or inactivation of a KR, DH or ER domain so that one or more of these functions is blocked and the strain produces a spinosyn having a lactone nucleus with a double bond, a hydroxyl group, or a keto group that is not present in the nucleus of spinosyn A (see Donadio et al., 1993); 2) replacement of an AT domain so that a different carboxylic acid is incorporated in the lactone nucleus (see Ruan et al., 1997); 3) addition of a KR, DH, or ER domain to an existing PKS module so that the strain produces a spinosyn having a lactone nucleus with a saturated bond, hydroxyl group, or double bond that is not present in the nucleus of spinosyn A; or 4) addition or subtraction of a complete PKS module so that the cyclic lactone nucleus has a greater or lesser number of carbon atoms. Example 5 illustrates use of mutagenesis to produce a spinosyn with modified functionality.

The DNA from the spinosyn gene cluster region can be used as a hybridization probe to identify homologous sequences. Thus, the DNA cloned here could be used to locate additional plasmids from the *Saccharopolyspora spinosa* gene libraries which overlap the region described here but also contain previously uncloned DNA from adjacent regions in the genome of *Saccharopolyspora spinosa*. In addition, DNA from the region cloned here may be used to identify non-identical but similar sequences in other organisms. Hybridization probes are normally at least about 20 bases long and are labeled to permit detection.

The modified strains provided by the invention may be cultivated to provide spinosyns using conventional protocols such as those disclosed in U.S. Pat. No. 5,362,634.

The following examples are provided in order that the invention might be more completely understood. They should not be construed as limitations of the invention.

EXAMPLE 1

Improved Yield of Spinosyns A and D by Transformation with Cosmid 9A6

Vegetative cultures of *S. spinosa* strain NRRL18538 were grown in 50 ml CSM medium (trypticase soy broth 30 g/l, yeast extract 3 g/l, magnesium sulfate 2 g/l, glucose 5 g/l, maltose 4 g/l) in 250 ml Erlenmeyer flasks shaken at 300 rpm at 30° C. for 48 h. Fermentation cultures contained a 1 ml inoculum of this vegetative culture in 7 ml of INF202, a proprietary medium similar to that described in Strobel & Nakatsukasa (1993). The cultures were grown in 30 ml plastic bottles arranged in 10×10 modules, shaken at 300 rpm in a 30° C. room for 3, 5 or 7 days. Broths were extracted with 4 volumes of acetonitrile, then analyzed for spinosyns A+D by isocratic high pressure liquid chromatography (HPLC) through a C-18 reversed-phase column (Strobel and Nakatsukasa, 1993). The amount of spinosyns was determined from absorbance at 250 nm. For each time point, spinosyns A+D were determined from 10 fermentation bottles. Two representative samples from each set of replicates were also analyzed by a slightly modified HPLC system for pseudoaglycone (PSA), the spinosyn precursor which lacks forosamine. In this system the mobile phase is 35:35:30 acetonitrile/methanol/0.5% (w/v) aqueous ammonium acetate (R. Wijayaratne, unpublished).

The cultures contain not only the insect-active spinosyns A and D, but also pseudoaglycone (Table 14).

TABLE 14

Spinosyn production in strain NRRL 18538

| Time | A + D (µg/ml) | PSA (µg/ml) |
|---|---|---|
| 3d | 101 ± 3 | 109 ± 11 |
| 5d | 269 ± 14 | 155 ± 26 |
| 7d | 334 ± 32 | 110 ± 53 |

The values are means±95% confidence levels. The accumulation of the pseudoaglycone, a forosamine-deficient precursor of spinosyn A, suggests that, in this strain grown under these conditions, the yield of spinosyns A+D is limited by the supply and/or addition of forosamine.

Cosmid 9A6 was conjugated from *E. coli* strain S17-1 (Simon et al., 1983) into *S. spinosa* strain NRRL 18538 using the method of Matsushima et al. (1994). Six independent isolates transformed with Cosmid 9A6 were subsequently grown and analyzed for spinosyn factor production under the fermentation conditions described above. The average yield of spinosyns A+D from these strains was higher than from their parent, by 35 µg/ml after 3 days of fermentation, and by 37 µg/ml after 5 days. The amount of pseudoaglycone in the transformed cultures was lower than in the parent strain throughout the fermentation (Table 15)

TABLE 15

Spinosyn production in derivatives of NRRL 18538 transformed with Cosmid 9A6.

| Time | A + D (µg/ml) | PSA (µg/ml) |
|---|---|---|
| 3d | 136 ± 4 | 31 ± 2 |
| 5d | 306 ± 5 | 7 ± 2 |
| 7d | 365 ± 7 | 7 ± 1 |

The values are means±95% confidence levels.

Strain NRRL 18538 and 6 independent isolates transformed with Cosmid 9A6 were analyzed for spinosyn content at different times during fermentation. For each strain, spinosyns A+D were determined from 10 fermentation bottles (Table 16). Two samples from each set of replicates were also analyzed for pseudoaglycone content (Table 17).

TABLE 16

Effect of Cosmid 9A6 on spinosyn A + D in NRRL 18538

| Time | −9A6 | +9A6 | Effect of 9A6 |
|---|---|---|---|
| 3d | 101 ± 3 | 136 ± 4 | +35% |
| 5d | 269 ± 14 | 306 ± 5 | +14% |
| 7d | 334 ± 32 | 365 ± 7 | +9% |
| 9d | 414 ± 17 | 411 ± 8 | −1% |

The values means in µg/ml±95% confidence levels.

TABLE 17

Effect of Cosmid 9A6 on pseudoaglycone accumulation in NRRL 18538

| Time | −9A6 | +9A6 | Effect of 9A6 |
|---|---|---|---|
| 3d | 109 ± 11 | 31 ± 2 | −72% |
| 5d | 155 ± 26 | 7 ± 2 | −95% |
| 7d | 110 ± 53 | 7 ± 1 | −94% |
| 9d | 119 ± 11 | 5 ± 1 | −96% |

The values are means in µg/ml±95% confidence levels.

It has therefore been demonstrated that transformation with Cosmid 9A6 can improve the efficiency with which precursor pseudoaglycone is processed to spinosyns. In NRRL 18538, the yield improvements for spinosyn A+D were 35% after 3 days of fermentation, and 14% after 5 days (Table 15). The rate-limiting process appears be the supply and/or addition of forosamine because pseudoaglycone was present in the parent at about 120 µg/ml throughout the fermentation, but in the transconjugants it was reduced to about 30 µg/ml at 3 days, and essentially depleted thereafter (Table 15). Although the conversion was not quantitative, the data are consistent with an improved efficiency in the processing of pseudoaglycone to spinosyn A+D in strains transformed with Cosmid 9A6. The effect could be the result of duplicating a forosamine biosynthetic gene, a forosaminyltransferase gene, or a combination of improvements. There was no statistically significant difference between the spinosyn A+D yields from the NRRL 18358 strains with or without Cosmid 9A6 after 7 or 9 days fermentation. Pseudoaglycone was still reduced in the transconjugants, but the extra spinosyn A+D produced by its conversion may not have been detectable against the higher background of spinosyns accumulated by this stage of the fermentation.

EXAMPLE 2

Correction of Methylation Deficiencies in Strain NRRL 18823 by Cosmid 9A6

Although spinosyn synthesis is limited by forosamine supply/addition in strain NRRL 18358, other biosynthetic functions may be limiting in other strains. *S. spinosa* strain NRRL18823 accumulates spinosyn H (2'-desmethyl-spinosyn A; Kirst et al., 1992), rather than spinosyn A. Spinosyn H is not an intermediate in the spinosyn A biosynthetic pathway, but a "shunt" product synthesized naturally when 2'-O-methylation does not occur. Cosmid 9A6 was conjugated from *E. coli* strain S17-1 into strain NRRL 18823 using the method described above. Two of the resulting exconjugants, when fermented, produced predominantly spinosyn A, with little spinosyn H (Table 18).

TABLE 18

| Strain | H (μg/ml) | A + D (μg/ml) |
|---|---|---|
| NRRL 18823 | 323 | 0 |
| NRRL 18823/9A6-2 | 36 | 551 |
| NRRL 18823/9A6-5 | 45 | 646 |

This shows that transformation with Cosmid 9A6 is able to overcome a second type of limitation to spinosyn production—the methylation deficiency in strain NRRL 18823.

EXAMPLE 3

Correction of 4'-O-methylation Deficiency in Strain NRRL 18743 by Cosmid 9A6

*S. spinosa* strain NRRL18743 accumulates spinosyn K (4'-desmethyl-spinosyn A), an intermediate in the spinosyn A biosynthetic pathway. Two of the exconjugants of strain NRRL 18743 containing Cosmid 9A6 produced predominantly spinosyn A, with little spinosyn K, while the third produced no detectable spinosyn K (Table 19).

TABLE 19

| Strain | K (μg/ml) | A + D (μg/ml) |
|---|---|---|
| NRRL 18743 | 488 | 0 |
| NRRL 18743/9A6-1 | 38 | 829 |
| NRRL 18743/9A6-2 | 22 | 725 |
| NRRL 18743/9A6-3 | 0 | 706 |

This demonstrates that transformation with Cosmid 9A6 is able to overcome a third type of limitation to spinosyn A production—the methylation deficiency in strain NRRL 18743.

EXAMPLE 4

Accumulation of Spinosyn Precursor Caused by Disruption of spnP

An internal fragment of spnP (bases 7391–8159) was amplified in a polymerase chain reaction using primers given in SEQ ID NO:34 and SEQ ID NO:35. AmpliTaq polymerase (Perkin Elmer, Foster City, Calif.) was used according to the manufacturer's instructions, in a 100 μl reaction with 20 pmoles of each primer and 1 μg of 9A6 DNA. The mixture was subjected to 25 cycles of 60 sec at 94° C., 60 sec at 37° C. and 120 sec at 72° C. The amplification product was cloned as an EcoR1-HindIII fragment into the plasmid vector pOJ260 (Bierman et al., 1992), then conjugated from *E. coli* S17-1 into *S. spinosa* NRRL 18538. Stable exconjugants, resulting from a single homologous recombination event between the plasmid-born and chromosomal sequences, contain a copy of the vector DNA integrated into the chromosome between two incomplete copies of spnP. When fermented, these exconjugants accumulate the forosamine-deficient precursor pseudoaglycones, rather than the end products spinosyns A and D (Table 20).

TABLE 20

| Strain | PSA (μg/ml) | A + D (μg/ml) |
|---|---|---|
| NRRL 18538 | 79 | 284 |
| NRRL 18538/1614-2 | 416 | 22 |
| NRRL 18538/1615-1 | 372 | 21 |
| NRRL 18538/1615-2 | 543 | 21 |
| NRRL 18538/1615-5 | 476 | 19 |
| NRRL 18538/1615-6 | 504 | 18 |

The pseudoaglycones are intermediates useful in the preparation of known insecticides (International Application WO 93/09126)

EXAMPLE 5

Accumulation of a Novel Spinosyn Following Modification of the PKS Domain ER2

Overlapping, complementary oligonucleotides SEQ ID NO: 36 and SEQ ID NO: 37 were designed to modify the gene encoding the enoyl reductase function in module 2 of the spinosyn PKS. These mutagenic primers provide for substitution of the sequence TCACC in place of GGTGG at bases 33563–33567 of SEQ ID NO:1, so that the sequence encodes a serine-proline dipeptide instead of a glycine-glycine dipeptide in the putative NAD(P)H-binding motif. A similar substitution was successfully used to inactivate an erythromycin ER without affecting any other PKS functions (Donadio et al., 1993). The substitution simultaneously introduced a novel PinA 1 restriction site, and eliminated a SgrA1 site, to facilitate detection of the engineered DNA in recombinant organisms.

Figure 5:
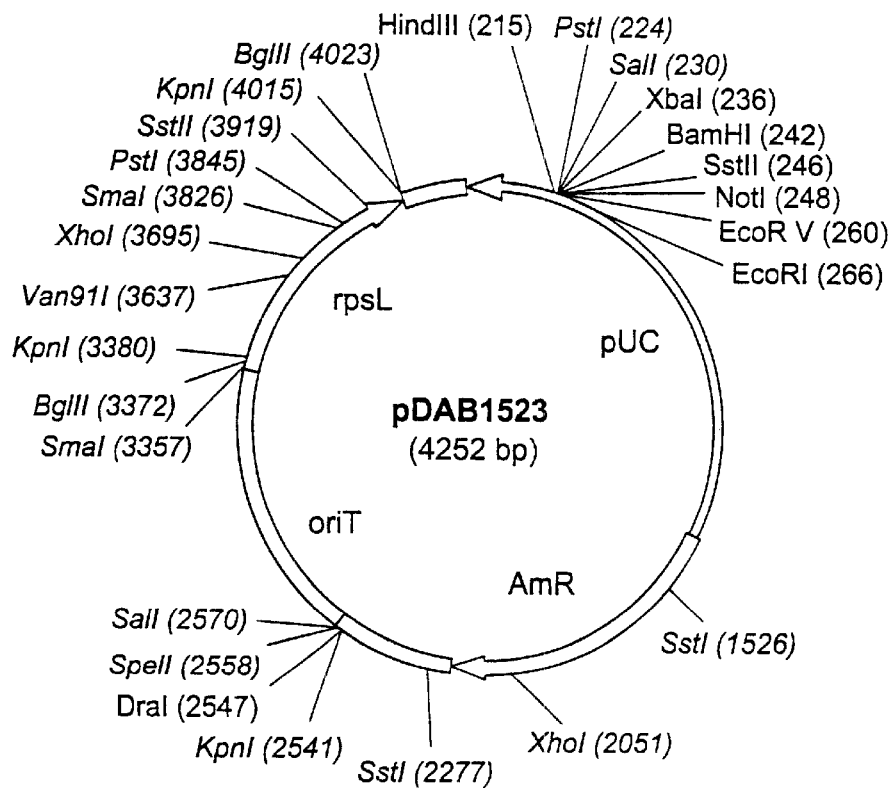
FIG. 5 is a restriction site and functional map of pDAB 1523.

In the first step of the mutagenesis, two separate PCR amplifications were performed, one using the mutagenic primer SEQ ID NO: 36 and flanking primer SEQ ID NO: 38, the other using mutagenic primer SEQ ID NO: 37 and flanking primer SEQ ID NO: 39. In the second step, the products of the first reactions were diluted 100-fold, pooled and amplified with only the flanking primers SEQ ID NO: 38 and SEQ ID NO: 39. In the third step, the products of the second PCR reaction were cloned into the plasmid pCRII according to the manufacturer's instructions (In Vitrogen, San Diego, Calif.). A portion of the mutated ER2 domain (spanning bases 33424–33626 in SEQ ID NO: 1) was excised as a Van911-NheI fragment, and inserted in place of the wild-type Van911-NheI fragment in a 3.5 kb EcoR1 fragment of cosmid 3E11 (bases 32162–35620 in SEQ ID NO: 1) cloned in the plasmid pbluescript SK- (Stratagene). The mutated EcoR1 fragment was then transferred into the conjugative plasmid pDAB1523 (FIG. 5), a derivative of pOJ260 containing the rpsL gene of *Streptomyces roseosporus* that confers a counter-selectable streptomycin-sensitive phenotype (Hosted & Baltz, 1997). The resultant plasmid containing the mutated EcoR1 fragment was conjugated from *E. coli* S17-1 (Simon et al., 1983) into SS15, a spontaneous streptomycin-resistant derivative of *S. spinosa* strain NRRL18538, using the method of Matsushima et al. (1994). (Spontaneous streptomycin-resistant derivatives of *S. spinosa* strain NRRL18538 can be readily isolated by those skilled in the art.) Apramycin-resistant exconjugants were shown to contain both wild-type and mutated versions of the ER2 domain by Southern hybridization with digoxygenin-labeled probes (Boehringer Mannheim). They also contained the *S. roseosporus* rpsL gene and consequently, on BHI agar (Difco, Detroit, Mich.) containing streptomycin at 150 mg/L, they grew poorly and failed to produce aerial mycelium. Spontaneous revertants to streptomycin-resistance were selected on the basis of their ability to grow and produce white, aerial mycelium on BHI agar containing streptomycin at 150 mg/L. Southern analysis indicated that these strains no longer contained the *S. roseosporus* rpsL gene or any other pDAB1523 sequences. Some strains had lost the entire cluster of spinosyn biosynthetic genes, including the ER2 domain, as well as pDAB 1523. In other strains the pDAB 1523 sequences had been excised along with the mutant ER2 domain, re-creating the parental gene structure. In a third type of streptomycin-resistant strain, the pDAB1523 had been excised with the wild-type ER2 domain, leaving the mutated version in its place. When fermented, a strain of this third type produced a novel metabolite, separable from spinosyn A by liquid chromatography on a C18 column (ODS-AQ, YMC, Wilmington, N.C.) using a mobile phase of acetonitrile: methanol: 2% ammonium acetate (44:44:12). The new entity was analyzed by electrospray ionization and tandem mass spectroscopy (Balcer et al., 1996) using a triple quadrupole mass spectrometer (TSQ700, Finnigan MAT, San Jose, Calif.). It had the properties expected of the C18:C19-anhydrospinosyn A, with a mass of 729.5 daltons and produced the 142 dalton forosamine fragment. We conclude that modification of DNA encoding PKS domains results in the production of novel fermentation products.

EXAMPLE 6

Improved Yield of Spinosyns A and D by Transformation of NRRL 18538 with Rhamnose Biosynthetic Genes Fragments containing the rhamnose biosynthetic genes were cloned independently into the conjugative vector pOJ260 (Bierman et al., 1992). The resulting plasmids are listed in Table 21.

TABLE 21

| Plasmid | Genes |
| --- | --- |
| pDAB1632 | gtt |
| pDAB1634 | gdh + kre |
| pDAB1633 | epi |

Each plasmid was conjugated from *E. coli* S17-1 (Simon et al., 1983) into *S. spinosa* NRRL 18538 by the method of Matsushima et al. (1994). Apramycin-resistant exconjugants, presumably containing a plasmid integrated into the chromosome by homologous recombination, were selected and fermented (Table 22).

TABLE 22

Spinosyn production in derivatives of NRRL 15328 transformed with rhamnose genes

| | Duplicated | A + D ($\mu$g/ml) | |
| --- | --- | --- | --- |
| Strain | Genes | Experiment 1 | Experiment 2 |
| NRRL 18538 | None | 344 ± 39 | 405 ± 25 |
| NRRL 18538/1632-1 | gtt | 410 ± 21 | 418 ± 38 |
| NRRL 18538/1634-1 | gdh + kre | 351 ± 27 | 360 ± 21 |
| NRRL 18538/1633-1 | epi | 318 ± 29 | 315 ± 18 |

The values are means±95% confidence limits.

In derivatives of NRRL 15328 transformed with gtt or epi, or the combination of gdh and kre, there was no consistent increase in the yield of spinosyns.

The fragments containing the gtt and gdh+kre genes were combined in a single plasmid. Two plasmids containing the combined gtt, gdh and kre genes (pDAB 1654 and pDAB1655) were isolated, and conjugated from *E. coli* S17-1 (Simon et al., 1983) into *S. spinosa* NRRL 18538 by the method of Matsushima et al. (1994). Apramycin-resistant exconjugants were selected and fermented (Table 23).

TABLE 23

Spinosyn production in derivatives of NRRL 15328 transformed with rhamnose genes

| | Duplicated | A + D ($\mu$g/ml) | |
| --- | --- | --- | --- |
| Strain | Genes | Experiment 1 | Experiment 2 |
| NRRL 18538 | None | 109 ± 9 | 133 ± 36 |
| NRRL 18538/1654-2 | gtt, gdh and kre | 323 ± 19 | 244 ± 34 |
| NRRL 18538/1654-5 | gtt, gdh and kre | 571 ± 23 | 412 ± 61 |
| NRRL 18538/1654-6 | gtt, gdh and kre | 577 ± 17 | 425 ± 51 |
| NRRL 18538/1654-11 | gtt, gdh and kre | 587 ± 23 | 426 ± 55 |
| NRRL 18538/1655-1 | gtt, gdh and kre | 501 ± 20 | 395 ± 59 |
| NRRL 18538/1655-3 | gtt, gdh and kre | 537 ± 27 | 421 ± 63 |
| NRRL 18538/1655-5 | gtt, gdh and kre | 529 ± 21 | 428 ± 47 |
| NRRL 18538/1655-12 | gtt, gdh and kre | 526 ± 26 | 401 ± 60 |

The values are means±95% confidence limits.

In derivatives of NRRL 15328 transformed with the gtt, gdh and kre genes, significant increases in spinosyn yields were observed. This probably results from overcoming a rate-limiting supply of NDP-4-keto-6-deoxy-glucose by simultaneously increasing the amounts of both gtt and gdh gene products, the enzymes necessary for its biosynthesis (see FIG. 1). A greater supply of the NDP-4-keto-6-deoxy-glucose intermediate would lead to increased production of both rhamnose and forosamine, and therefore greater ability to convert aglycone to spinosyns A+D. Consistent with the hypothesis that deoxysugar supply is limiting spinosyn production in NRRL 18538, many mutants blocked in forosamine synthesis or addition accumulate PSA to very high levels. More of this intermediate can be made because it requires only one deoxysugar, compared with the two required for spinosyns A or D.

The present invention is not limited to a particular vector comprising spinosyn genes of the invention, but rather encompasses the biosynthetic genes in whatever vector is used to introduce the genes into a recombinant host cell.

In addition, due to the degeneracy of the genetic code, those skilled in the art are familiar with synthetic methods of preparing DNA sequences which may code for the same or functionally the same activity as that of the natural gene sequence. Likewise, those skilled in the art are familiar with techniques for modifying or mutating the gene sequence to prepare new sequences which encode the same or substantially the same polypeptide activity as the natural sequences. Consequently, these synthetic mutant and modified forms of the genes and expression products of these genes are also meant to be encompassed by the present invention.

All patents and publications referred to above are incorporated by reference herein.

REFERENCES

1. Altschul, S. F., W. Gish, W. Miller, E. W. Myers, and David J. Lipman (1990). Basic local alignment search tool. *J. Molec. Biol.* 215:403–10.
2. Aparicio, J. F., I. Molnar, T. Schwecke, A. Konig, S. F. Haydock, L.E. Khaw, J. Staunton & J. F. Leadlay (1996). "Organization of the biosynthetic gene cluster for rapamycin in *Streptomyces hygroscopicus*: analysis of the enzymatic domains in the modular polyketide synthase," *Gene* 169: 9–16.
3. Balcer, J. L., S. M. Brown & D. F. Berard (1996). "A rapid screening technique for identification of Spinosad photolysis products using ESI/MS/MS," *Proc. 44th Conf. Amer. Soc. Mass Spec.*
4. Baltz, R. H., M. A. McHenney, C. A. Cantwell, S. W. Queener & P. J. Solenberg (1997). "Applications of transposition mutagenesis in antibiotic producing streptomycetes," *Ant. van Leeuw.* 71:179–187.
5. Bibb, M. J., P. R. Findlay & M. W. Johnson (1984). "The relationship between base composition and codon usage in bacterial genes and its use for the simple and reliable identification of protein-coding sequences," *Gene* 30: 157–166.
6. Bierman, M., R. Logan, K. O'Brien, E. T. Seno, R. N. Rao & B. E. Schoner (1992). "Plasmid cloning vectors for the conjugal transfer of DNA from *Escherichia coli* to Streptomyces spp," *Gene* 116: 43–49.
7. Broughton, M. C., M. L. B. Huber, L. C. Creemer, H. A. Kirst & J. A. Turner (1991). "Biosynthesis of the macrolide insecticidal compound A83543 by *Saccharopolyspora spinosa*," Ann. Mtg. Amer. Soc. Microbiol.
8. Burgett, S. G. & P. R. J. Rosteck (1994). "Use of dimethyl sulfoxide to improve fluorescent, Tag cycle sequencing in *Automated DNA sequencing and analysis*,". M. Adams, C. Fields & J. C. Venter, eds. NY, Academic Press: pp. 211–215.
9. Dehoff, B. S., S. A. Kuhstoss, P. R. Rosteck & K. L. Sutton (1997). "Polyketide synthase genes." EPA 0791655.
10. Don, R. H., P. T. Cox, B. J. Wainwright, K. Baker & J. S. Mattick (1991). "Touchdown' PCR to circumvent spurious priming during gene amplification," *Nucl. Acid Res.* 19: 4008.
11. Donadio, S., J. B. McAlpine, P. S. Sheldon, M. Jackson & L. Katz (1993). "An erythromycin analog produced by reprogramming of polyketide synthesis," *Proc. Natn. Acad. Sci. USA* 90: 7119–7123.
12. Donadio, S. & L. Katz (1992). "Organization of the enzymatic domains in the multifunctional polyketide synthase involved in erythromycin formation in *Saccharopolyspora erythrae*," *Gene* 111: 51–60.
13. Donadio, S., M. J. Staver, J. B. McAlpine, S. J. Swanson & L. Katz (1991). "Modular organization of genes required for complex polyketide biosynthesis," *Science* 252: 675–679.
14. Fish, S. A. & E. Cundliffe (1997). "Stimulation of polyketide metabolism in *Streptomyces fradiae* by tylosin and its glycosylated precursors," *Microbiology* 143: 3871–3876.
15. Geistlich, M., R. Losick, J. R. Turner & R. N. Rao (1992). "Characterization of a novel regulatory gene governing the expression of a polyketide synthase gene in *Streptomyces ambofaciens*," *Mol. Microbiol.* 6: 2019–2029.
16. Hosted, T. J. & R. H. Baltz (1997). "Use of rpsL for dominance selection and gene replacement in *Streptomyces roseosporus*", *J. Bacteriol.* 179: 180–186.
17. Inouye, M., H. Suzuki, Y. Takada, N. Muto, S. Horinouchi & T. Beppu (1994). "A gene encoding mycinamicin III O-methyltransferase from *Micromonospora griseorubida*," *Gene* 141: 121–124.
18. Jiang, X. M., B. Neal, F. Santiago, S. J. Lee, L. K. Romana & P. R. Reeves (1991). "Structure and sequence of the rjb (O antigen) gene cluster of Salmonella serovar typhimurium (strain LT2)," *Mol. Microbiol.* 5: 695–713.
20. Kirst, H. A., K. H. Michel, J. S. Mynderse, E. H. Chio, R. C. Yao, W. M. Nakatsukasa, L. D. Boeck, J. L. Occlowitz, J. W. Paschal, J. B. Deeter & G. D. Thompson (1992). "Discovery, isolation and structure elucidation of a family of structurally unique, fermentation-derived tetracyclic macrolides, in *Synthesis and Chemistry of Agrochemicals III*," D. R. Baker, J. G. Fenyes & J. J. Steffens, eds. Washington, D.C., American Chemical Society: pp. 214–225.
21. Linton, K. J., B. W. Jarvis & C. R. Hutchinson (1995). "Cloning the genes encoding thymidine diphosphoglucose 4,6-dehydratase and thymidine diphospho-4-keto-6-deoxyglucose 3,5-epimerase from the erythromycin-producing Saccharopolyspora erythraea."
22. Liu, H. W. & J. S. Thorson (1994). "Pathways and mechanisms in the biogenesis of novel deoxysugars by bacteria," *Ann Rev Microbiol* 48: 223–256.
23. Matsushima, P., M. C. Broughton, J. R. Turner & R. H. Baltz (1994). "Conjugal transfer of cosmid DNA from *Escherichia coli* to *Saccharopolyspora spinosa*: effects of chromosomal insertion on macrolide A83543 production," *Gene* 146: 39–45.
24. Ruan, X., et al.(1997). "Acyltransferase Domain Substitutions in Erythromycin Polyketide Synthase Yield Novel Erythromycin Derivatives," *J. Bacteriology* 179, 6416.
25. Siggard-Andersen, M. (1993). "Conserved residues in condensing enzyme domains of fatty acid synthases and related sequences," *Protein Seq. Data Anal.* 5: 325–335.
26. Simon, R., U. Preifer & A. Puhler (1983). "A broad host range mobilization system for in vivo genetic engineering: transposon mutagenesis in Gram negative bacteria," *Bio/Technology* 1: 784–791.
27. Solenberg, P. J. & S. G. Burgett (1989). "Method for selection of transposable DNA and characterization of a new insertion sequence, IS493, from *Streptomyces lividans*," *J. Bacteriol.* 171: 4807–4813.
28. Strobel, R. J. & W. M. Nakatsukasa (1993). "Response surface methods for optimizing *Saccharopolyspora spinosa*, a novel macrolide producer," *J. Ind. Microbiol.* 11: 121–127.
29. Thorson, J. S., S. F. Lo & H. Liu (1993). "Biosynthesis of 3,6-dideoxyhexoses: new mechanistic reflections upon 2,6-dideoxy, 4,6-dideoxy, and amino sugar construction," *J. Am. Chem. Soc.* 115: 6993–6994.
30. Weber, J.M. & J.B. McAlpine (1992). "Erythromycin derivatives," U.S. Pat. No. 5,141,926.

We claim:

1. An isolated DNA molecule comprising a DNA sequence that encodes a spinosyn biosynthetic enzyme, wherein said enzyme is defined by the amino acid sequence of SEQ ID NO:8.

2. An isolated DNA molecule of claim 1 wherein said DNA sequence is SPnG gene, said gene being described by bases 18541–19713 of SEQ ID NO:1.

3. A recombinant DNA vector which comprises a DNA sequence as defined in claim 1.

4. A host cell transformed with a recombinant vector as claimed in claim 3.

5. A process for isolating macrolide biosynthetic gene probes, which method comprises (a) creating a genomic library of a macrolide-producing microorganism;

(b) hybridizing a labeled polynucleotide to the genomic library wherein said polynucleotide is SEQ ID NO:1, bases 18541–19713; and (c) isolating fragments that hybridize to said polynucleotide wherein said fragments are at least 20 bases long and are macrolide biosynthetic gene probes.

6. A process of claim 5 wherein the microorganism is a spinosyn producing microorganism.

* * * * *

UNITED STATES PATENT AND TRADEMARK OFFICE
CERTIFICATE OF CORRECTION

PATENT NO. : 6,521,406 B1
DATED : February 18, 2003
INVENTOR(S) : Richard H. Baltz et al.

It is certified that error appears in the above-identified patent and that said Letters Patent is hereby corrected as shown below:

Column 41,
Line 48, "SPnG" should read -- spnG --.

Signed and Sealed this

Twelfth Day of August, 2003

JAMES E. ROGAN
*Director of the United States Patent and Trademark Office*

SEQUENCE LISTING

<160> NUMBER OF SEQ ID NOS: 39

<210> SEQ ID NO 1
<211> LENGTH: 80161
<212> TYPE: DNA
<213> ORGANISM: Saccharopolyspora spinosa

<400> SEQUENCE: 1

| | | | | | |
|---|---|---|---|---|---|
| gatctccatg | aagctcaacg | taggcacgga | cggtcaggtg | gactgggtga | tcgcccgcga | 60 |
| cctgctggcc | gacgggctga | tcgccgaggc | aggcgaaggc | gatgtgcgga | tcggccctcg | 120 |
| acggggtttt | ccggggttgg | tcgtgatcga | gatgagctcg | ccgtcgggc | aggcctcctt | 180 |
| cgaggtgaat | gctgaccagc | ttgcggactt | cttgaacgac | acctacgacg | tggtcgaacc | 240 |
| tggtgatgaa | caccggtgga | tgaacgtcga | cgaggtgctg | agccagctgc | tctcgccaac | 300 |
| ctgtaatggc | ccagctctcc | cgaagcgccg | cacgccaaag | cgctggctgc | gggacctggc | 360 |
| ggcgctgaac | accgccacgc | tgtgtctccg | agctccagct | ggaccacgtc | ggtgccgtgc | 420 |
| gcccggctcg | gtcaggccga | aggtgctgat | cttctccagg | cgcgccatcg | gcgcaggaag | 480 |
| cgctgcttct | gctcccgccg | cagtaccgtc | gtgtcatggc | cacggacagc | ttcgattcct | 540 |
| cgaagctaca | ggcggccgtg | gcatcgagcg | tcgcgtcgtg | cgtctcggaa | gtcagccgag | 600 |
| acgtctacac | gcacctgatt | accgaggctc | cgcagttgcg | agccgatgag | atcgtcctca | 660 |
| gcattctacg | gacgagtgtt | gaggaaaata | tcgccacatt | gccgcacgtt | ctcgaattcg | 720 |
| agattccgtt | gggatattcg | ccgggtcctg | ctgcggtgtt | ggagtatccg | cgacgactgg | 780 |
| cgaaacattt | ccatcaacgc | gctgatcagg | gccaaccgca | tcgggcactt | ccgcttcctg | 840 |
| tagtgatgcc | tcgacgagat | ccgccgccaa | tgcgccgacg | aggccgtatc | cgcagcgacc | 900 |
| acgcaacgaa | tgctcgcaac | cagcttcggc | tacatcgacc | gcgtcacgga | gcagatcgcc | 960 |
| gaaacctacc | agctcgaacg | ggaccgctgg | ctcctggcga | cgggacggcc | gtgaggtctc | 1020 |
| tgcggcatcc | gcatagcgtc | ttctcccgct | gaggcacatg | aggtgttgcg | cgcggtcgtt | 1080 |
| tccggcagtc | gcacggcatt | cgtcctagct | gcgggcaatt | gagggagcga | agatttagag | 1140 |
| gagtgtggcc | acgcggacca | agccggcgag | tgctcgggag | cggctgtggg | gcggccaggc | 1200 |
| gatgactgtc | gtcacgtccg | gcgcgtctag | aaccggtacg | gcggcgaggc | cttcgagcag | 1260 |
| gttgacgcga | ctggattcgg | gcatgaccac | ggtagtgcgg | ccgagtgcga | tcatttggaa | 1320 |
| cagttgcgtc | tggttgcgta | cttccacgcc | ggggccatct | ggatagacgc | cgtcggggcc | 1380 |
| gggccagcgc | gcaagcggga | gatccggcag | tgagctgaca | tccgccatcc | gtacatgggg | 1440 |
| ctcgctggca | agcggatgcg | aggtcggaag | aatggcgact | tgttgctcgg | tgttcagaat | 1500 |
| ttcgatgtcg | agttcggccg | tcgggtcgaa | gggttgatgc | aacagcgcca | cgtcggcccg | 1560 |
| gccgtcatgc | agcgttttct | ggggctggga | ttcgcagagc | agcaggtcga | cggccacggc | 1620 |
| tcccggctcg | gcggcgtacg | cgtcgagcaa | cttcgccagc | agctcaccgg | aggcgccggc | 1680 |
| cttggcagcc | aggactagcg | agggctggct | cgtcgcggca | cgctgggtgc | gtcgctcggc | 1740 |
| tgctgccagc | gcgccgagga | tcgcccgccc | ttcggtcagc | agcattgccc | cggcttcggt | 1800 |
| gagcgagact | ttgcggctgg | tgcgttgcag | caacacgact | ccgagtcgtt | gctcgagctg | 1860 |
| ggcgatcgtc | cgcgacagcg | gcggctgggc | gatgccagg | cgctgggcgg | ccggccgaa | 1920 |
| gtgcaactcc | tcggcgactg | caacgaagta | ccgcaactcc | cgcgtctcca | tccgtcgagc | 1980 |
| ctaccgctga | ttcatatcag | ctgggtatcg | gtgtgagacc | tagatggtgt | tggttccccg | 2040 |

-continued

```
ccggtttcgg gccacgctag aaagcatgag cgaacagacg attgcactgg tcaccggcgc    2100
aaacaaggga atcggatacg agatcgcggc cgggctcggc gcgctgggt ggagcgtcgg      2160 aatcggggca cgggaccacc agcgcgggga ggatgccgtg gcgaaattgc gtgcggacgg    2220
cgtcgatgcg ttcgcggtat ccctggacgt gacagacgac gcgagcgtcg cggctgctgc    2280
ggctctgctc gaggagcgcg ccggccggct cgatgtgctg gttaataacg ccggcatcgc    2340
cggggcatgg ccggaggagc cctcgaccgt cacaccggcg agcctccggg cggtggtgga    2400
gaccaacgtg atcggcgtcg ttcgggttac caacgctatg ctgccgttgc tacgccgctc    2460
cgagcgcccg cggatcgtca accagtccag ccacgtcgct tccctgacct tgcaaaccac    2520
gccgggcgtc gacctcggcg ggatcagcgg agcctactca ccgtcgaaga cgttcctcaa    2580
cgcgatcacc atccagtacg ccaaggaact cagcgatacc aacatcaaaa tcaacaacgc    2640
ctgccccggc tacgtcgcga ccgaccttaa cggcttccac ggaaccagca cgccggcaga    2700
cggtgccagg atcgccattc ggctcgccac gctgccagac gacggcccga ccggaggcat    2760
gttcgacgac gccgggaatg tgccctggtg aggcgctcag tcggcgatgg tgcaatcgaa    2820
gtcggagagg ctcgctgcga ccgggtacgc cgaacaacac ctgttcctgt gggtacggat    2880
gtcggccttc gccgtctcgg tcattgacaa cctgtacttc gggcgccgtt accgccggtg    2940
cgccgcggtt gcctggcgac actgggccag ccgtggctca ccggcggctt aggtcaggcg    3000
tgggcggttg ccagcatggc gggtgcggct ttgcgtaggt cgggtaggcg catccggcgc    3060
gggagccggt cgagttcttc gccgatggcc ggtgctttgg ggctgctcag gagccgaaca    3120
cctcccagcc gcaggtgccg ggctgaaccg agtggttctc gtcggctcgg atcacaacgt    3180
ctgccggaac agctgcggcg aggtggtcgc agattcgagg cgggatcgtc ctcggcgacc    3240
ttgccgacga tcgcggctag ggcccagggc ttcgtcgacc tggttggcac ctagatcacg    3300
acggtcaaaa cttgccggca tcagagacga tcgaagtgat cccgggtcac gtcggcttat    3360
cggtcgagtg agtcccgggg cctgcccagc caggtcttgc gtcgttgttc cgggctcagt    3420
tgcggattcc gacgaacagg cctcggccgt tcggtgctcc aggaaggtat tccgcgcgga    3480
tccctgcgtc ttcgagcgcg gcggtgtact cgtcctcagt gaacagcgag aggatttcga    3540
actctgtgaa gtcccggatc ccggtgggtt cggcgactgt gtagcggacg tcatccggc    3600 tcgtacggcc ctccaggacc gagtgcgata gccggctgat cacccgctcg ccgtggtgcg    3660
cgacggctcc ggtgacgaac ccgtcgatga acttgtcggg aaaccaccag ggttcgatga    3720
ccgcgactcc accaggggcc aggtgccggg ccatgttccg cgtcacgcgt cgcaggtcgt    3780
caacggtccg catgtaagcc gcggtaaagc acaggcaggt gatgacgtcg aatggctcgc    3840
cgaggtcgaa atcgcggatg tcaccgatgt gaatcggtac ctcagggact cgtctgatcg    3900
cgatctcccg catcgcatcg gacagttcaa gccccgcgac cttcgcgtat tcggcacgga    3960
atcgctctag gtgcgccccg gtcccacagg cgacgtcgag tagggactgt gcttcgggca    4020
gcctggtgcg tacgagctgg actacttccc cggcctcggc tgcccagtcc cggccacgcg    4080
cggagtggat cgcgtcgtag atgtcggcat gatctggct gtataccgag gaggtttctg    4140
cgaatgtgtc gctcacgcgc gacatcctca ctttcggagt ggtgatcttt ggctgatgtg    4200
gtgttcgacg gccttctgga actcgtcagc caccgtgcgc acctcggcgt cgtcaaggct    4260
tgggtgcagt ggtagcagga gtgttctgcg gcaggcgtcc tccgcagaag gcagcttgca    4320
gtccgcgcgg tagatgggga ccttgtgcag gggcgggtag cggtagctcg tgtagatgcc    4380
```

```
gcgttccagc atttgctgcg ccacctggtc gcggatctcc ggagccagct ggacccagta    4440
gaagtagtgt gacgagacgt gcccatccgg tagcgtcggc ggtaggagga cacccggcac    4500
atcggaaagc aaccggtcgt actgcgtagc gatttctcta cgcctgttga tgaattctgg    4560
cagtttgcgc agctgcacgc tgccaagcgc tgccgtcatg tcgttcccga tcagccgctg    4620
gccgatgtct tcgacgcgaa tatcccacca gcggttggaa gacttggccg aatcgaatcc    4680
gctcatctgc tcaagaccgt ggtaggcgag tcgtcttgcg cggtgcgcca gctccggatc    4740
cgccgcgtag aacatgcccc catccccggt gaccaggatc ttcatcgcat cgaaactcca    4800
cgtggccagg tcaccaaagg ttccgcaagc ggtgccgtgc acggacgatg ccaccgcgca    4860
ggcggagtcc tcgatgagca tgaggcccct tcacggcag aaatcggcga tcgcggtgac    4920
ttctcccggc gatcctccat agtggagcag caatacggcc ttggtcgccg gcgtgatggc    4980
cctcgccaca tcatccagcg tggggttcaa cgtccggggg tcgacgtcgc agaacaccgg    5040
gcgggcaccg gaggatgcga tggcgttggc cgccgccacg aagcttatcg aaggaagtac    5100
cacgtcgtcg cctgggccga ggtcgagcac ctgcacggta aggaacagcg cggcagtccc    5160
cgagttgagg aacacgacct gttcgggatc cactcccagg tggtgggcga attcggcctc    5220
gaacgtccgg gtgcgcggcc cgagcccgat ccagttggag gcgaacacct ccgcgatcgc    5280
gtcgagttct tcggtgccga ggatcggctg gtgcaggttg atcacgttgc tgaaatcctc    5340
cgagatgccg ccatgctgga tgctaggaac tcttggccac gaattcagcg attgattcga    5400
cgacgtagtc gatcatttgg tccgttatgc ctgggtagac gccgacccag aaggttcggt    5460
cggtgacgat gtcgctgttg gtgagcgcgt cggcgatccg gtaccgcacc tgctcgaagg    5520
ccgggtgccg ggtgatgtta ccgccgaaca gcagtcgggt gccgatgttg cgggattcca    5580
ggaagttcac caggcggca cgggtgaacc cggcgtccgc actgatggtg atcgcaaacc    5640
cgaaccagct cgggtcgctg tgcggtgtgg ctaccggcag cagcaggccc ggcaacccgg    5700
acagcccttc gcgcaaccgt cgccagttac ggcggcgtgc cgacccgaat gcggaaatct    5760
tgctcaactg gctcagcgca agtgcggcct gcaggtcggt ggtcttgagg ttgtaaccga    5820
cgtgggagaa cgtgtacttg tggtcgtagc ccggtggaag ggtaccgagg tggtagtcga    5880
acctcttgcg gcaggtgttg tccacgccgg gctcgcacca gcaatcccgt ccccagtcac    5940
gcagcgactc gatgatgcga gccaattcca ggctgccggt caacacgcag ccaccctcgc    6000
cgctggtgat gtgatgggca ggatagaagc tgacgttgt caggtcgccg aaggttccgg    6060
tcagccgtcc ccggtaggtg gatcccaccg catcacagtt gtcttcgacg aggaacagct    6120
cgtgttcttt tgcgatctcc gcgatttcgt cagcggcgaa ggggttgccc agggtgtgcg    6180
ccagcatgat ggctcgcgtc cgttccgtga cggcggcctt gatgcggtct ggcgttgcgt    6240
tgtaggtgcc cagttccacg tcgacgaata ccgggacgag tccgttttgg accgccggat    6300
tgatcgtcgt ggggaagccg accgccgcag tgatcacttc gtcgccgggc cgcagtcgtg    6360
cctcgccgag tttgggggag gtaagcgaac tcagtgccag gagattggcc gacgaaccgg    6420
agttgacgag atgagccttg cggaggccga agaagcgggc gaactcgctc tcgaatcgcc    6480
gtgcattccc gcccgcggcg atccggagct ccagcgcggc ttccaccagt gccaccggt    6540
cgtcctcgtc gagcacggcg cccgatggcc ggatcggcgt cgatccagcc acgaaggtcg    6600
gggattcctg ttcgcggtgg taatcgcgta cggatgccaa tatccggtcc ttggcatccg    6660
gcaccatctc agtagcggta gcgcaagtgt cgtcacacga agtcactctg gcgcgcccctt    6720
tccccagcgc tctggttttc cggctctgca tgcaggcgac gatcagtctt cgcgccttgc    6780
```

```
cttcaggaga tgagcgatgc ccgtggcgaa tcgcgttatg acgtcccagc gggacagtgt   6840
gctgtctcgg cgccttacac cttcctgccc tggttcgatg cggtgcggga catcaggaca   6900
gcggagcaag gagaagcgct cattgactca gaaatcctcg atctacccgg cacacccgac   6960
tcggtagagc ccaggctagc gggaacgacc tgctcgcgct tgtcaagatc gctaccatca   7020
cctggaaggc ctaagatttg gcttgcgaaa gcggcgtttc ccgggggata tcagagattt   7080
ctgtgattct tggcatgctt cccgggtgtt caattgcgat cggagagttc atgcgtgtcc   7140
tgttcacccc gctgccggcg agttcgcact tcttcaacct ggtgccgttg gcgtgggcgt   7200
tgcgtgccgc ggggcacgag gtccgtgtcg ccatctgccc gaatatggtg tcgatggtca   7260
ccggagcagg actcaccgcg gttcccgtcg gcgacgagct cgacctcatc tccttggcgg   7320
ccaagaacga actcgttctc ggcagcgggg tctcgttcga cgagaagggg cggcatccgg   7380
aactcttcga cgagctgctg tcaatcaact ccggcagaga cacggacgcc gtggagcaac   7440
tccaccttgt ggatgaccga tcgctggacg atctcatggg gttcgccgag aaatggcagc   7500
ctgatctcgt tgtgtgggac gctatggtgt gttcggggcc agttgtggcg cgagcgctcg   7560
gcgcacgaca cgtgcggatg ctcgtcgccc tcgatgtgtc ggggtggctg cggtccggtt   7620
tcctcgaata ccaggaatcg aagccgcctg agcagcgcgt cgacccgctc gggacgtggc   7680
tgggagcgaa gctcgccaag ttcggagcca cgttcgatga agagatcgtg acgggccaag   7740
cgaccataga tccgattcca tcctggatgc gcctgcctgt ggacttggac tacatctcga   7800
tgcgtttcgt gccgtacaac ggtccggcgg tgttgccgga gtggttgcgc gaacgaccga   7860
cgaagccgcg cgtctgcatc acgcgcgggc tgaccaagcg gcggctgagc agggtgaccg   7920
aacagtacgg ggagcaaagt gaccaggaac aagcaatggt ggaaaggttg ttgcgcggcg   7980
cggccaggct cgacgtcgag gtgatcgcca ccttgtctga cgacgaagta cgggagatgg   8040
gggagttgcc ctcgaacgtc cgggtccacg aatacgtacc gctcaacgaa ctgctggagt   8100
cgtgttcagt gatcatccat catggctcga cgacgacgca ggaaaccgcc acggtcaacg   8160
gcgtaccgca gttgattctc cctgggacct tctgggacga atctcgtagg gcggagctcc   8220
tagccgatcg gggagccggt ctggtcctcg accccgcgac gtttaccgaa gacgacgtgc   8280
gaggtcagct ggcccgcctg ctcgacgagc cgtcgttcgc tgccaacgcg gcgctgatcc   8340
gccgtgaaat cgaggaaagt cccagcccgc acgacatcgt tccacgtctg gaaaagctag   8400
ttgccgaacg tgagaaccgc cgcactgggc agtctgatgg ccatccgtga gcaacgtgtg   8460
gccggaaaca tggacgccgg ggtttggcag gtgttcatcg ctgttgcgtc gactcggatt   8520
ccgccgtgac cgggacgatg ccaggcgagt cccgaagtca gattcttgtc cagaatcgtc   8580
caatggggtg ttgatctccc cagaggtttg cgctccaacc gatttccgac gaggatcgtg   8640
gcgcccgctg agcaacgact accgtgcggt cgagacatac cgctgtgcgc caggagcgaa   8700
ggtgggttgc ccgatcaccg tgctggtggt agatgccgag ccgaaggtca ccttggatga   8760
ggcggaagcc tggcgagagc acaccgaggc cgtggccgac gtccgtgtct tctccggcgg   8820
gcatttcttc atgaccgaac gccaggacga ggtgctcgcg gtccttacgg gcggatcgct   8880
tcgatgatcc tcgccaggcc gctggaccag accgcgacgc cctgggagc cggcgtgcac   8940 atcgtcacgg cagtgaggga ttgggcatga gcagttctgt cgaagctgag gcaagtgctg   9000
ctgcgccgct cggcagcaac aacacgcggc ggttcgtcga ctctgcgctg agcgcttgca   9060
atggcatgat tccgaccacg gagttccact gctggctcgc cgatcggctg ggcgagaaca   9120
```

```
gcttcgagac caatcgcatc ccgttcgacc gcctgtcgaa atggaaattc gatgccagca    9180
cggagaacct ggttcatgcc gacggtaggt tcttcacggt agaaggcctg caggtcgaga    9240
ccaactatgg cgcggcaccc agctggcacc agccgatcat caaccaggct gaagtaggta    9300
tcctcggcat tctcgtcaag gagatcgacg gcgtgctgca ctgcctcatg tcagcaaaga    9360
tggaaccggg caacgtcaac gtcctgcagc tctcgccgac ggttcaggca actcggagca    9420
actacacgca ggcacaccgt ggcagcgttc cgccctatgt ggactacttc ctcgggcggg    9480
gccgcggccg cgtgctggta gacgtgctcc agtctgaaca ggggtcctgg ttctaccgga    9540
agcgcaaccg gaacatggtg gtggaagtcc aggaggaagt gccagtcctg ccagacttct    9600
gctggttgac gctcggccag gtgctggctc tccttcgtca ggacaacatc gtcaacatgg    9660
acacccggac ggtgctgtct tgcatcccgt tccacgattc cgccaccgga cccgaactag    9720
ccgcctcgga ggagcccttc cgacaggcgg tggccaggtc gctctcgcac ggcatcgatt    9780
cgtcgagtat ctccgaggcg gtcggttggt tcgaggaagc caaggcccgc taccgcttgc    9840
gggcaacgcg cgttccgctg agcagggtcg acaagtggta tcgcaccgat accgagatcg    9900
cccaccagga cggcaagtac ttcgcggtga tcgcggtgtc ggtgtccgcg accaatcgtg    9960
aggtcgccag ctggacgcag ccgatgatcg aaccgcgaga acaaggtgag atcgcactgt   10020
tggtcaagcg gatcggcgga gtgctgcacg gtttggtcca cgctcgggtg gaggctgggt   10080
ataagtggac tgcggaaatc gctcccacgg tccagtgcag tgtggccaac taccaaagca   10140
ccccgtcgaa cgactggccg ccgttcttgg acgacgtgct caccgccgat cccgaaaccg   10200
tgcggtacga atcgatcctg tccgaagaag gcggtcggtt ctaccaggcg cagaacaggt   10260
accggatcat cgaggtgcat gaggacttcg cggcacgacc tcccagcgac ttccggtgga   10320
tgactttggg acagttgggc gagctgctcc ggagcaccca cttcttgaac atccaggcgc   10380
gcagcttggt cgcctcccctg catagcttgt gggcgttggg gcgatgacca gctcgatgcg   10440
aaagccggtg cgcatcggtg tgctcgggtg cgcttccttc gcgtggcgac ggatgctgcc   10500
cgcgatgtgc gacgtggccg aaacagaggt ggtggcggtg cgagccgtg atccggcgaa   10560
agccgaacgg ttcgcagcgc gattcgaatg cgaggcggtg ctgggttacc agcggctcct   10620
ggagcggccg gacatcgatg ccgtctacgt gccgttgccg cctggcatgc atgcagagtg   10680
gatcggcaag gcgcttgagg cagacaaaca cgtgcttgcg gagaaaccgc tgacgacgac   10740
ggcgtccgac accgctcgcc tggtcgggct ggccaggagg aagaacctgc tgctgcggga   10800
gaattacctg ttcctccacc acggccggca cgacgtggtc cgcgacctgc tgcaatccgg   10860
ggagatcggt gagctccggg agttcaccgc cgtgttcgga attccgccgc ttcccgacac   10920
ggacatccgc tatcgcaccg aactcggtgg cggagcgttg ctggacatcg tgtctatcc   10980
cgcccgtgcc gctcggcact ttctcctcgg tccgctcacg gttctcggcg caagctcgca   11040
cgaggcccag gagtcgggcg tcgacttgtc gggcagcgtg ctgctccaat cggaaggtgg   11100
caccgttgcc cacctcggat acggtttcgt gcaccactac cgcagcgcgt acgagctgtg   11160
ggggagtcgt gggcgaatcg tcgtcgaccg ggcgttcacg ccgcccgccg agtggcaggc   11220
cgtgatccga atcgagcgga agggcgttgt cgacgagttg tccttgccag cggaagatca   11280
ggttcgcaag gcggtcaccg ccttcgcacg cgacatcaga gcagggacag gcgtggacga   11340
ccctgcggtg gccggagatt cgggcgaatc gatgatccag caggccgcgc tggtggaggc   11400
gatcggtcag gcccgtcggt gcgggtccac atagccgccc ggcatccgcg ggtagtagtt   11460
cgcctcgaag cctgaccggg catccggaag ccagcgggga agccgctgga gaggctcacc   11520
```

-continued

```
gccatccgct cacctggcat ctcgcggacc gctgatcgcg gacggctcgg agaagtgctc    11580
gtcgaaccac gagacgacca ctcgcgagct ggccagggcg gcgggaaagt gagccaatcc    11640
ggagagcgga tgccaccgca ctggcgtacc cgccgcgcgg tagctgtccc ggagtcgctc    11700
gccgaatgcg aacggaacga tctcgtcgtc cgtgctgtgg tagacgagcg tgggaccac     11760 cgggccaccg ttcctacctg cgacgctttc ggccagtcgt gcgcgccatc gaggttgctc    11820
gaaaaggccg gaagtgtcga ggaagtcgct cagctcgcgg ccgaggaagc gggtgacgag    11880
ctccggtgca ccgagctcgc gcacttgatc aacggcggta cgacccgctt cggtgagaag    11940
ctcgtcgaat ggcagatcgg ggtaggcagc ggcatgcccg accaggccgg ccagcaccgg    12000
cccggtgaac accccgtcat ttcggtggat gatgtccagc agatcgatcg gcaccgcacc    12060
tgcggccgca gcgcggattc gcagttcagg tgcgtaggtg gggtgcagtt cgccggcgaa    12120
ggccgacgct tgcccaccct gcgcatagcc ccagatgccg accgggcagt cggtcgtcag    12180
gccggagccc ggtagccgtt gcgcagcgcg ggcggcatcg agcatggcgt gtccctgcgc    12240
cctgccgacg tgtaggtgt gggttccagg agtaccgagg ccttcgtagt cggtgatgac     12300
cacggcccac ccgcggtcga gggccacggc gatcagctcg gtctccggct cggttccggt    12360
tcgaagcagg tacgacgggg caacttggct accgaggccg tgggtgccca ctgcgaaagt    12420
gatgatgggg cgatcttcgc gcggccacgg gatgttcggc accagaacgg tgccggagac    12480
ggcgttcggc atgccaaggg cggagttgga ccggtagagg attgccagg ccttggctgc     12540 gacgggttcg cccgtgccgc gcagtgccga gacgggccgg gccctgagga gcgtgcccgg    12600
gacacccggg ggtagcggcg tcggcggtcg gtagaaggga tcatccgcgg gtgcccgcag    12660
atcgtcgccg accaggctgg cgtgctcgga ggccatcagg actgcttctt tcgagcctgc    12720
aggagcatga aacccatgct ttcctcgttt ctggcgtaat ccggatgttt ccggtattcc    12780
gcaaccgcgg cgatcagctg tgctggtccc ggtccgtgct tcgccgcgat gtctcccaag    12840
tagcgttgct ggtaggtgcc gacagccgca ggctcgacgc cggcgagctc atcgagtttc    12900
cggagcaact cgtcgacgta ccaggagacc atgcacctgg tctgtgccgt gaggtcggtg    12960
acttcgagaa tctcgaaccc ggcttcgctg accagcgccg tgaagctgtt caaggtatgg    13020
gcggtcgtgc ccgtccaaac cgccgcgtac tcttccggga gtcgaacccg agtgatgatg    13080
tctccgagga cgaaccggcc gccgggttcc aggattcggt ggacctcgcg gatcgcggcg    13140
gcctggtcca cgatctgcac gacggactgc atcgcccatg cggcctgaaa gaaaccgtcc    13200
gggtagggca gctgggcgcc gtcgactaga tcgaactcaa gactgccggc cagtccggtc    13260
tcgttggcga gcctggtggc ggcggcgaga tgctgggcgt tcacggtgat tccggtgact    13320
cgaacgccgc tggcgcatgc cgcacggact acgggctgcc cattgccgca gcccaggtcg    13380
aacaggtgcg ctccgggacg gagcgcggcc ttgtcgatga acaggtcggt cagttggtcg    13440
gcagcatccg accacggtgt ggcaccggca tcctcccgat acccgcccgc ccagtaaccg    13500
tggtgcaggg gacgcccgtg cgccaacgca tcgaagatgg actccacctg atccgcggtc    13560
ggaaatgcct gtgtgttcgc ccctctgctg ttcactcgtc ctccgcgctg ttcacgtcgg    13620
ccaggtgcaa tatgtcgtcc agactccttg gcacccaagc aggaacgccg ccttcggcgt    13680
tgacgccttt ctccaggaac gcgatgttgt ggtaggtgtg gaggccgacc aaattgcgtt    13740
ccaggtagct cggctcgtac gagcccgcat gcggctgctc ctcgtgctga acgccttcca    13800
acaggttctt gagcaggctg accgtggtgc cgggtgcggc cgggcactgc gcctgcccgc    13860
```

-continued

```
cgaatccggg agcataggtc gtccacagat cctcgatcac gtatacgcca ccgctgcgca    13920
accgggggaa cagcgtttcc agggatgtgc gcacgtgtcc gttgatgtgg ctgccatcgt    13980
cgatgatgat gtcgaacggt ccgtacttgt cgtcaacggc ggccagctcc tcgggcttgc    14040
tctggtcggc gcggacggtg cagagcctct gctggtcgag gaaggacttg tcgaaaacgt    14100
ccatcccgaa cacgaggccg cggtggaagt agcgcttcca catcttcagg gattcgccgc    14160
cgccaccgtc gaagttgtag ccaccgacac cgatctccag gatgcgcacc gggcgatcac    14220
ggaactcgcc gaggtgtcgc tcgtatagcg gggtgaacca gtgcaggccg ccccacttgt    14280
ccgtgcggta gtgggaggcg agcaagttga ggtcgggacg tcggtgcccg cagccggcga    14340
ccactgcgga gatggcctgg aagccatcgg acagttccga cggaccgggt atcgaaccgg    14400
atgtggtggt tcggaggaag ttggtgctcc gggcgccgac ggccctggga gctcctgggc    14460
cgaacaactc ggcgatgaga tcggtgagct cgtaaccgat ccgcagcggg acgtctccga    14520
ccggtcgttg ctcggccttg atcagctcac cggactgtag cgtcaggacg aagtcaacgg    14580
tctcgcctcg gtgggtgatc tggaccgcga cctcggtccg ttcgatgtcg ggggccggtt    14640
ccgcgcggaa gaggatctcg tcgatcagca cgggtgcgat cctggcgagt ccgagttcgg    14700
tggtcaggtc ggccaggctc gccgcactgg atccggcggc gaggatgatg cgttccacgg    14760
tttcgatctc gtgcgttgtg gacatcgtga tgagctcctc atggctgacc gggtgaaagc    14820
cgtgccggcg gtttgatcga caggccgtgc tggaagatgt tctgcggatc ccaccgcgct    14880
ttggcccgct gcagccgcgg gtagttgtct ttgtagtaca ggtcgtgcca ggcaacaccg    14940
gaggtgttcc acaatggatc ggccaagtcg gtgtccgggt agttgatgta ggagccgtcg    15000
acacgggtac ctggcaccgg aactccgccg gtttcggcgt acatctcgcg gtagaaaccg    15060
cgaatccagg tcagatgccg ctcgtcctcg gcgggctccg accagttcgt gacgaacagc    15120
gctttgagaa ccgagtcgcg ctgagcgagt gcggtggccg acggagccac ggcattcgcc    15180
ataccgccgt aaccgagcag caacagcgcc gccgcagggt tgtcgtatcc gtagacggtc    15240
```